(12) United States Patent
Roberts

(10) Patent No.: US 10,436,765 B2
(45) Date of Patent: Oct. 8, 2019

(54) SYSTEMS, APPARATUS, AND METHODS FOR IDENTIFYING SPECIES IN POTENTIALLY TIME-VARYING MIXTURES OF FLUIDS

(71) Applicant: Restream Solutions, LLC, Galveston, TX (US)

(72) Inventor: William Roberts, Galveston, TX (US)

(*) Notice: Subject to any disclaimer, the term of this patent is extended or adjusted under 35 U.S.C. 154(b) by 0 days.

(21) Appl. No.: 15/294,407

(22) Filed: Oct. 14, 2016

(65) Prior Publication Data
US 2017/0241930 A1  Aug. 24, 2017

Related U.S. Application Data

(60) Provisional application No. 62/296,901, filed on Feb. 18, 2016.

(51) Int. Cl.
*G01R 27/28* (2006.01)
*G01N 33/28* (2006.01)

(52) U.S. Cl.
CPC .................. *G01N 33/2823* (2013.01)

(58) Field of Classification Search
CPC ........ G01N 27/02; G01N 27/06; G01N 27/08; G01N 27/041; G01N 27/046; G01N 27/048; G01N 27/223; G01N 27/121; G01N 27/07; G01N 27/9046; G01N 33/2888; G01N 33/2823; G01N 33/2858; G01N 17/02; G01N 17/04; G01B 7/003; G01B 7/023; G01D 5/202; G01R 27/02; G01R 31/022; A61B 5/0537; A61B 5/4872; A61B 5/0424; A61B 5/053

USPC ........ 324/230, 634, 640, 643, 689, 692–699
See application file for complete search history.

(56) References Cited

U.S. PATENT DOCUMENTS

| | | | | |
|---|---|---|---|---|
| 5,353,627 A | * | 10/1994 | Diatschenko | G01N 29/036 73/19.03 |
| 5,589,057 A | * | 12/1996 | Trimble | B01J 8/003 208/148 |
| 6,919,034 B2 | * | 7/2005 | Kozak, III | B01D 17/00 210/799 |
| 2003/0134426 A1 | * | 7/2003 | Jiang | E21B 47/011 436/121 |

(Continued)

*Primary Examiner* — Thang X Le
(74) *Attorney, Agent, or Firm* — Geoffrey A. Mantooth; Brian K. Yost

(57) ABSTRACT

Systems, apparatus, and methods for sensing species in fluids. In accordance with some embodiments, methods comprise activities such as diverting of the fluid into an analytics spool. These methods also comprise causing the fluid to separate into layers. Furthermore, they comprise sensing the type of fluid flowing at a position where water is likely to flow. Some methods further comprise sensing a pressure, a temperature, and a total dissolved solids concentration in the fluid. Moreover, such methods can comprise comparing those conditions to precipitation curves for a plurality of species. These methods can also comprise determining whether a particular species might be precipitating from the fluid. Some methods comprise sensing a carbon dioxide and an oxygen concentration in the fluid. Moreover, such methods can comprise determining whether a ratio between the carbon dioxide and oxygen concentrations has changed. Additionally, or alternatively, such methods can comprise sensing a hydrogen sulfide concentration.

20 Claims, 7 Drawing Sheets

(56) References Cited

U.S. PATENT DOCUMENTS

| | | | |
|---|---|---|---|
| 2010/0313964 A1* | 12/2010 | Hin | C02F 1/006 137/15.01 |
| 2013/0146388 A1* | 6/2013 | Ao | G01N 29/2462 181/175 |
| 2014/0331785 A1* | 11/2014 | Ao | G10K 11/00 73/861.18 |
| 2015/0218010 A1* | 8/2015 | Benavides | C02F 1/001 210/741 |
| 2015/0348395 A1* | 12/2015 | Trout | G08B 21/20 340/605 |
| 2015/0361350 A1* | 12/2015 | Prasad | G05D 7/0676 700/285 |
| 2016/0097106 A1* | 4/2016 | Robinson | C23F 11/08 514/44 R |
| 2016/0201439 A1* | 7/2016 | Peitz | E21B 43/24 137/334 |
| 2016/0202709 A1* | 7/2016 | Newman, Jr. | G05D 9/12 137/2 |
| 2016/0313237 A1* | 10/2016 | Young | G01N 21/31 |

\* cited by examiner

SYSTEMS, APPARATUS, AND METHODS FOR IDENTIFYING SPECIES IN POTENTIALLY TIME-VARYING MIXTURES OF FLUIDS

CROSS REFERENCE TO RELATED APPLICATIONS

This application is a non-provisional application of, and claims priority to, U.S. provisional patent application No. 62/296,901 entitled Production Fluid Monitoring Device, filed on Feb. 18, 2016, filed William Roberts, the entirety of which is incorporated herein as if set forth in full.

BACKGROUND

American energy independence, a goal that is tantalizingly close as of this writing, depends to a large extent on the ability of the United States to produce oil (and/or other hydrocarbons) in large quantities at low cost. While hydrofracturing ("fracking") and other drilling technologies have dramatically reduced the cost of producing such hydrocarbons, the complex and time-varying chemistry of produced hydrocarbons can decrease the production of any given well (or group of wells) and can even cause a well to be shut down for maintenance/re-stimulation, work-overs, or shut-in permanently should conditions deteriorate far enough.

More specifically, such time-varying chemistry presents a number of technical problems. For instance, certain species in the produced fluid can cause corrosion in the well, the wellhead, production equipment, transportation pipelines, gathering facilities, and other points downstream therefrom. Moreover, hydrogen sulfide dissolved (or released) in the produced fluid can present an environmental and/or safety hazard (as well as contributing to some modes of corrosion). Bacteria in the fluid can foul filters, coat sensors, and contribute in their own ways to corrosion. Salts and other chemicals can precipitate out of solution and coat the internal surfaces of various components with scale, thus leading to decreased throughput, inaccurate sensor readings, reduced heat transfer capabilities, etc. Similarly, asphaltenes, paraffin's, hydrates, and/or the like can precipitate from the produced fluid thereby clogging pipelines and/or fouling many types of equipment.

Corrosion, which is often characterized by a loss of metal (or other materials) due to chemical (and/or electrochemical) reactions can eventually degrade and/or destroy structures in the production systems. Corrosion can occur anywhere in these systems, from the bottom of the "hole" (and any tools located therein) up to and including surface-based lines and/or equipment. The corrosion rate(s) will vary with time depending on the particular conditions of the oil field/systems such as the amount of water produced, secondary recovery operations, and pressure, temperature, and/or chemical concentration variations.

Hydrogen sulfide (H2S) presents another problematic chemical/corrosion issue often associated with produced fluids. At low concentrations, H2S has the odor of rotten eggs, but at higher, lethal concentrations, it is odorless. Accordingly, H2S is hazardous to workers with even a few seconds of exposure at relatively undetectable concentrations (by human senses) sometimes being lethal. But even exposure to lower concentrations can also be harmful to personnel with chronic exposure being associated with a number of health issues.

H2S can also cause sulfide-stress-corrosion cracking metals. Because it is corrosive, the presence of H2S in produced fluids can require costly countermeasure such as using high-quality alloys, stainless steel (and/or other, more exotic materials) for tubing and the like. Such sulfides can be treated chemically, provided that they are detected in a timely fashion. More specifically, the sulfides can be precipitated from water, muds, oils, and/or oil muds by treating them with a sulfide scavenger. Follow up testing with (for instance) a Garrett Gas Train can also be conducted to determine sulfide concentrations in the treated fluids. Moreover tests can indicate the need/desire for caustic soda treatments to raise the fluid's pH and/or the need/desire for zinc-based scavengers to remove sulfides (in the form of ZnS).

Moreover, some produced fluids and/or "muds" host sulfur reducing bacteria (SRBs) and/or other so-called biologics. These anaerobic bacterium (the SRBs) can convert sulfate ions such as SO4-2 into S-2 and HS—, with the concomitant oxidation of a carbon source to H2S. The lignite, lignin, tannins, cellulose, starches, fatty acids, and other organic species found in many produced fluids and/or muds provide carbon based food sources and mineral nutrients for such SRBs. Accordingly, produced fluids can have high (and time-varying) SRB concentrations. Moreover, H2S combined with iron can form iron sulfide, a scale that is very difficult to remove.

SRBs, furthermore, occur naturally in surface waters, including seawater and other potential contamination sources that might be introduced into a well for various purposes (for instance as fracking water). Of course, other biologic species can present corrosion issues as well. Thus, bacteria accumulation can lead to pitting of steel and/or buildups of H2S which increases the corrosiveness of the water (and/or other fluids), thereby increasing the possibility of hydrogen blistering and/or sulfide stress cracking which can result in integrity failures and unintended release of hydrocarbons/produced fluids into the environment.

Before storage of hydrocarbons, muds, fluids, and/or other materials potentially containing SRBs, treatment with a bactericide can inhibit SRB growth. Also, circulating these fluids from time to time, with air injection/entrainment, can retard development of anaerobic conditions which favor the growth of SRBs. In situations in which aerobic biologics are found, blanketing the fluids/muds with an inert gas can retard the growth/propagation of these biologic species but only if they are detected and identified in a timely manner.

Produced fluids can also contain materials which lead to scaling of internal surfaces. Many scales form from mineral salt deposits that may occur in the produced fluids. In many situations, a produced fluid is (or becomes) saturated with certain chemicals during its travel through the various systems disclosed elsewhere herein. More specifically, the fluid might travel from a regime in which the pressures, temperatures, pH, etc. preclude precipitation in any meaningful amount to a regime in which one or more factors have changed leading to saturation conditions and thus precipitation of one or more scale-producing species.

With relatively severe conditions, scale can create a significant flow restriction, or even a plug, in a production system. While scale removal is a common well-intervention operation (with a wide range of mechanical, chemical and scale inhibitor treatment options available), it still introduces labor and consumable costs. Moreover the scale removal additives can affect the chemistry of the produced fluid (for instance altering its pH) which in turn leads to other chemistry related issues (for instance, fostering SRB growth). Additionally, it should be noted that scale-precipitation events are variable in nature, and will typically manifest themselves in a non-static fashion as temperature, pressure, and contaminant concentrations vary over time and in response to discrete events. Again, though, corrective measures depend on timely identification of the potentially problematic species in the comingled fluids.

Asphaltenes paraffins hydrates, and other similar precipitating species can present still other issues for the well operator, owner, and/or other users. For instance, paraffins are hydrocarbon compounds that often precipitate on/in production components as a result of the changing temperatures and pressures within these systems. Heavier paraffins occur as wax-like substances that may build up on internal surface/components and can restrict (or even stop) production flowrates. Paraffins are normally found in the tubing close to surface. Nevertheless, it can form at the perforations of the well casing, or even inside the formation, especially in depleted reservoirs or reservoirs under gas-cycling conditions. Asphaltenes and hydrates present similar issues as those caused by paraffins.

Moreover, the presence of many of these species mask each other's presence. Thus, the comingled species in produced hydrocarbons present a number of chemistry related problems that, for efficient, reliable operation of a system ought to be detected so that they can be dealt with. However, heretofore available systems cannot reliably detect much less identify the various species in comingled fluids in many processes.

SUMMARY

The following presents a simplified summary in order to provide a basic understanding of some aspects of the disclosed subject matter. This summary is not an extensive overview of the disclosed subject matter, and is not intended to identify key/critical elements or to delineate the scope of such subject matter. A purpose of the summary is to present some concepts in a simplified form as a prelude to the more detailed disclosure that is presented herein. The current disclosure provides systems, apparatus, methods, etc. for identifying species in potentially time-varying mixtures of fluids and more particularly for identifying species in fluids produced by hydrocarbon wells and adjusting the chemistry of those fluids and the mechanism by which accessory equipment may be used to bring those fluids to market.

For decades, fixed-rate chemical application programs have been applied to oilfield fluids with fluctuating chemistries. This approach leads to inefficient chemical dosing, and asset management schemes, which can adversely impact well production and equipment longevity. Embodiments disclosed herein provide operators with real-time, on-site fluid chemistry and dynamics monitoring as well as automated chemical application/addition processes. Systems of embodiments described herein are available from ReStream Solutions, LLC of Galveston, Tex. under the Pro Stream Fluid Monitoring package line of products.

Systems of embodiments can be installed at points throughout overall hydrocarbon production processes. For instance, they can be installed at upstream locations, midstream locations, and downstream locations. At upstream locations such systems help users manage drilling, and fracking (or otherwise stimulating), completing and/or producing hydrocarbon wells. These systems also assist users in managing production chemistry, flow assurance, and/or well monitoring. At midstream, systems of embodiments identify when and where problematic conditions might be developing/occurring as comingle fluids flow through various pipelines. In locations further downstream, systems can help with corrosion management, process optimization, regulatory compliance, etc. among other activities (as well as increasing equipment longevity).

Embodiments provide hardware/software packages that are designed to increase well productivity and maintain production equipment/hardware via novel, non-obvious, and innovative approaches to 1) production monitoring, 2) production management, and/or 3) chemical treatment application. Some systems feature plug-and-play suites of integrated analytical sensors, pressure transducers, temperature transducers, power measurement devices and flowmeters, coupled to onboard CPUs (central processing units), to monitor production fluid characteristics and subsequent well productivity responses to chemical, operations and/or workover regimens. Systems of the current embodiment can be deployed at wells, and/or can be used to monitor corrosion and/or restrictive conditions in midstream and/or upstream applications.

As data is collected and analyzed by systems of the current embodiment, chemical dosing regimens, recommended preventive maintenance, equipment operation, and well servicing initiatives (for instance, soap-stick applications) can be automatically adjusted in real-time to maximize system performance and/or increase equipment longevity. The data collected by these systems is streamed to (centralized) servers (via on-board cellular modems or other transmitters) where it is further stored, analyzed and used to develop more successful management practices for incorporation into the packages. Such capabilities allow for individual (and local group) well production enhancement practices to be systematically deployed across common geographic areas and similar reservoir formations. The collection of multiple analytic values as a function of time, stimuli, and/or well productivity allows for the characterization of down-hole fluid dynamics that can be used to maximize product yield in accordance with embodiments. Data collected on the servers of embodiments allow for comparative well analysis, more accurate modeling, and/or potential reservoir yield forecasts.

Furthermore, "fluid fingerprinting" is an approach incorporated into systems of various embodiments to accurately characterize fluid properties and, subsequently, and if desired, to mitigate potential chemistry-related issues. With systems heretofore available there is no way for operators to know what type of scale is forming, where it is forming, and/or whether the chemical treatment regime they are using to manage it is actually working. However, by comparing fluid analytical values, pressure deltas, temperatures, and/or recorded laboratory data (thus, "fingerprinting" the fluid) systems of the current embodiment can identify when, where and what type of scale will be formed (and/or has been formed or is forming). Such systems can monitor and/or evaluate the rate of anti-sealant dosed to determine whether the dosage is actually working. Such systems can also automatically increase/decrease the dosage as necessary to minimize the potential for scale to form. Thus, fluid fingerprinting allows systems to "see" more of what is in the fluids and how those fluids respond to different stimuli.

The benefits of real-time monitoring for pipelines/flowlines are multi-faceted. For one thing, in many cases, issues associated with corrosion, scale, biofilm accumulation, etc. do not happen as a result of a single, catastrophic event. They are more often the result of many, relatively smaller events (for instance, occasional poor separator operation through swings in oil/water cut percentages) which create an environment that allowing these issues to proliferate. However, if a user's strategy to combat these issues is doing grab samples and essentially taking snap-shots of a pipeline's fluid chemistry values at discrete moments in time, it is almost impossible to identify when, where and/or why problems are occurring because the conditions causing them are often transient. Additionally, in the case of pipelines, these processes can make it difficult to pinpoint which operators/operations are most responsible for providing low-quality fluid.

Real-time monitoring in accordance with embodiments reduces or eliminates such conditions. It also, moreover, allows for the identification of trends associated with fluid dynamics and/or chemistry performance which would typically be overlooked by human operators. Real time monitoring (for the identification of potentially problematic conditions) and the ability to compile the real-time data over time, allow for much more comprehensive picture of when, where and/or why issues are occurring, and how to best mitigate those issues to maximize system efficiency and/or profitability.

Embodiments provide apparatus configured to fingerprint fluid flowing from hydrocarbon wells which potentially include time-varying mixtures of gases, hydrocarbons, water, and/or various other species therein. Apparatus of the current embodiment comprise analytics spools, flow control devices, conductivity sensors, and controllers in communication with the conductivity sensors. The flow control devices are configured to divert a flow of fluid into the analytics spools which are shaped and dimensioned such that the fluid flowing therein separates into layers of materials with differing densities. At least some gases typically separate from the fluids due to pressure drops whereas some of the hydrocarbons and water separate due to the shapes and dimensions of the analytics spools (which causes the velocity of the fluids to slow substantially). As to the conductivity sensors, they are positioned in the analytics spools at positions and at heights at which (mostly) water is likely to being flowing. Moreover, the conductivity sensors are configured to sense the conductivity of the fluids flowing at those positions and are further configured to generate signals indicative thereof. The controllers, meanwhile, are in communication with the conductivity sensors and are configured to, determine whether the fluids flowing at the positions of the conductivity sensors are water responsive to signals from the conductivity sensors.

Moreover, in various embodiments, the apparatus also comprises a pressure sensor, a temperature sensor, and a conductivity sensor all positioned at an approximately common position along the analytics spool and being in communication with the controller. The controllers of the current embodiment are configured to identify pressure and temperate "points" (at the common positions) responsive to corresponding signals from the pressure and temperature sensors. The controllers, furthermore are configured to compare the pressure and temperature points to a plurality of precipitation curves for a corresponding plurality of species which are potentially in the fluid. The controllers are further configured to determine whether the sensed total dissolved solids have changed and to output indications responsive thereto that particular species might be precipitating from the fluids.

Apparatus of various embodiments comprise analytics spools, flow control devices, sensors, and controllers. The flow control devices divert fluid into the analytics spools which are configured such that the fluids therein separate into layers of differing densities. The sensors are positioned in the analytics spools to sense the types of fluids flowing at the positions corresponding to the sensors and to generate signals indicative thereof. Regarding the controllers, they are in communication with the sensors and with the flow control devices and are configured to output signals indicative of the types of fluids flowing past the sensors.

In some apparatus of the current embodiment, the sensors are conductivity sensors which are mounted on the analytics spool at a clocked position with the analytics spools further comprising additional clocked positions adapted to receive the conductivity sensors. In addition, or in the alternative, the fluids can be mixtures of hydrocarbons and water. Furthermore, some apparatus further comprise temperature, pressure, and/or total dissolved solids sensors in the analytics spools and/or upstream/downstream thereof. Indeed, some of these sensors can be located at wells which provide the fluid flows. These sensors are in communication with the controllers which compare the pressures and temperatures and precipitation curves for species (which might be in the fluids) and to determine therefrom which species might be precipitating from the fluids.

If desired, the apparatus comprise pH sensors, oxidation reduction potential sensors, conductivity sensors, oxygen sensors, and corrosion sensors. Furthermore, some apparatus of the current embodiment comprise carbon dioxide and oxygen sensors. In these apparatus, the controllers compare the signals from the carbon dioxide and oxygen sensors to determine whether the ratios of carbon dioxide and oxygen are changing over time. In the alternative, or in addition, some apparatus further comprise hydrogen sulfide sensors and/or bacteria traps which can capture biologic species which might be in the fluids. Further still, in some embodiments, the apparatus further comprise pumps which boost the pressures of the fluids in the analytics spools.

Apparatus of some embodiments further comprise interfaces which receive signals from wells indicative of the pressures, flow rates, and temperatures of the fluids flowing from the wells. In these embodiments, the controllers compare the signals from the well sensors with corresponding signals from sensors (downstream) in the apparatus. Moreover, these apparatus may further comprise total dissolved solids/conductivity sensors. The controllers sense changes in the total dissolved solids concentrations and determine (from the comparisons of the wells and corresponding downstream signals) which species might have precipitated out of the fluids between the well and downstream sensors. Furthermore, and if desired, some apparatus further comprise corrosion sensors and sensors configured to sense potential biological activity. The controllers of these embodiments are further configured to determine whether corrosion (sensed by the corrosion sensors) is biological in nature.

In accordance with some embodiments, methods of fingerprinting a fluid flowing from a hydrocarbon well are provided. Such methods comprise activities such as diverting a portion of the fluid into an analytics spool. These methods also comprise causing the fluid to separate into layers of differing densities due to the shape and/or dimensions of the analytics spool. Furthermore, they comprise sensing a type of fluid flowing at a position along the analytics spool where a layer of water is likely to flow using a sensor. Additionally, and in accordance with the current embodiment, the methods also comprise outputting a signal indicative of the type of fluid at the position using a controller which is in communication with the sensor.

Some methods in accordance further comprise sensing pressures, temperatures, and total dissolved solids concentrations at approximately common positions relative to the analytics spools using corresponding sets of sensors. Moreover, such methods further comprise identifying, responsive thereto, pressure and temperature points at the common positions using the controllers and comparing the pressure and temperature points to a plurality of precipitation curves for a corresponding plurality of species (that are potentially in the fluids). These methods may also comprise determining whether the sensed total dissolved solids concentrations have changed using the controllers and outputting indications responsive thereto that particular species might be precipitating from the fluids using the controllers.

Furthermore, some of these methods further comprise changing positions of the sensors responsive to the sensed types of fluids. In the alternative or in addition, such methods can comprise sensing pH, oxidation reduction potential, conductivity, oxygen concentration, and/or corrosion rates in the fluids using corresponding sets of sensors. If desired, these methods can also comprise sensing carbon dioxide and oxygen concentrations in the fluids using corresponding pairs of sensors. Moreover, such methods can comprise determining whether ratios between the carbon dioxide and oxygen concentrations have changed (or are changing) and outputting signals indicative thereof. Additionally, or alternatively, such methods can comprise sensing a hydrogen sulfide concentrations in the fluids and outputting indications thereof.

To the accomplishment of the foregoing and related ends, certain illustrative aspects are described herein in connection with the annexed figures. These aspects are indicative of various non-limiting ways in which the disclosed subject matter may be practiced, all of which are intended to be within the scope of the disclosed subject matter. Other advantages and novel and non-obvious features will become apparent from the following detailed disclosure when considered in conjunction with the figures and are also within the scope of the disclosure.

BRIEF DESCRIPTION OF THE FIGURES

The detailed description is described with reference to the accompanying figures. In the figures, the left-most digit(s) of a reference number usually identifies the figure in which the reference number first appears. The use of the same reference numbers in different figures indicates similar or identical items.

DETAILED DESCRIPTION

Figure 1:
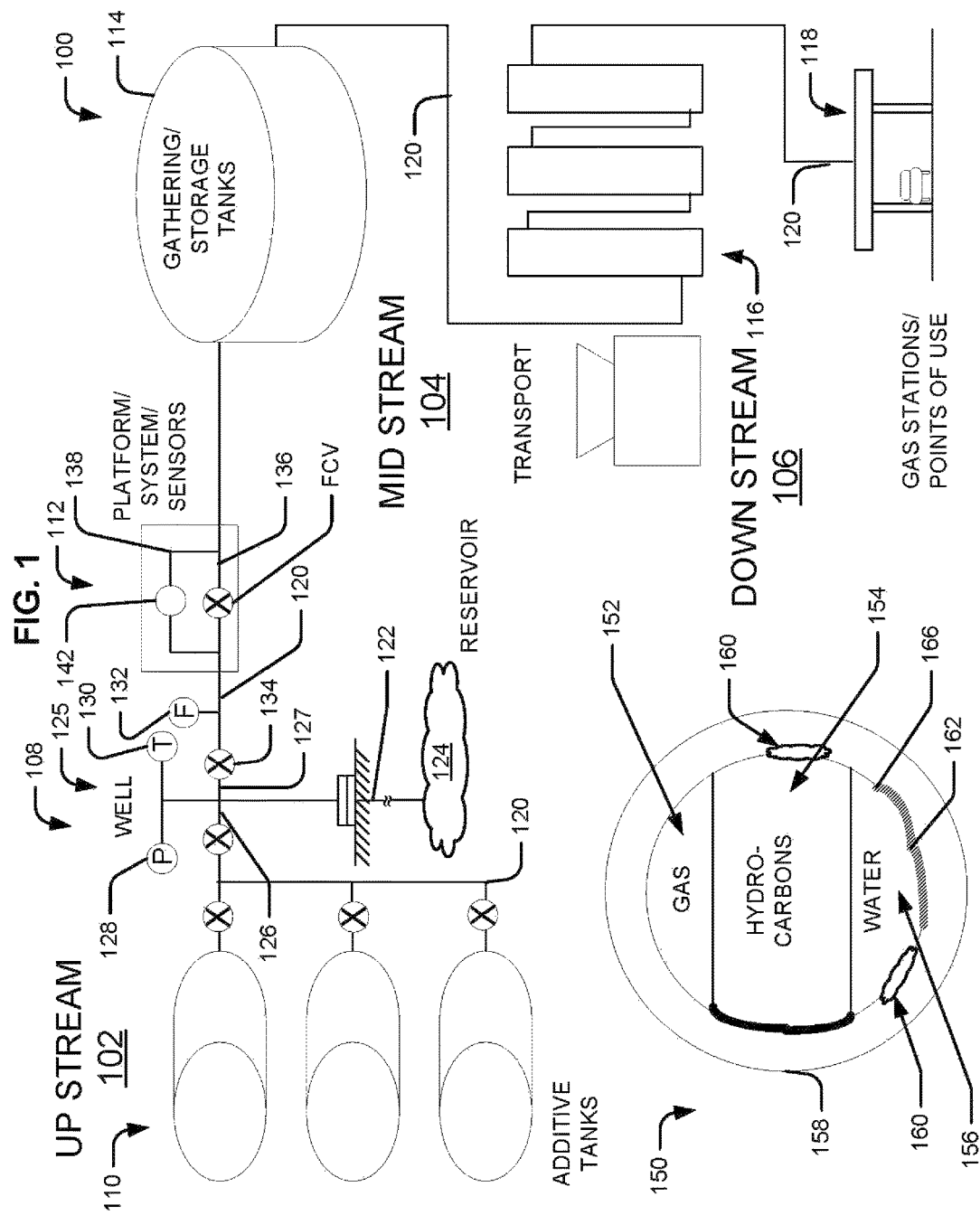
FIG. 1 illustrates an integrated process system.

The current disclosure provides systems, apparatus, methods, etc. for identifying species in potentially time-varying mixtures of fluids and more particularly for identifying species in fluids produced by hydrocarbon wells and/or adjusting the chemistry of those fluids.

Systems of embodiments are designed to measure/monitor process fluid chemistries and fluid dynamics of oilfield fluids in real-time. These systems are engineered to maximize the efficiency and longevity of the sensors utilized so that the system can operate for extended periods of time without maintenance/servicing. The sensors onboard these platforms/systems are selected to not only provide accurate data in harsh environments, but to also provide data that could be used to characterize fluid behavior, fluid chemistry, and process trends.

In accordance with embodiments, systems allow for (inter alia) the following:
  Real-time collection of process variables of interest
  Logging/transmission of variable values to remote database(s)
  Identification of potentially problematic conditions within the process fluids and/or associated machinery
  Management of potential problems by user alerts and/or for real-time chemical application or equipment operation.

Systems of the current embodiment use the following sensors:
  High pressure/annulus pressure—Pressure measurements prior to introduction into the surface systems, and/or before any controlled pressure drops. In the current embodiment these pressure transducers are mounted to measure the annulus pressures of the wells.
  Line pressures/system input pressures—these pressure measurement points are located at the inputs to surface systems of the current embodiment. They allow tracking of the incoming pressures to these systems and measurement of the pressure drops from the high pressure transducers (there are typically chokes or backpressure valves located immediately before the well flowlines).
  Discharge pressure/system output pressures—These pressure measurement points are located at the discharges of the systems. They allow for tracking the pressure deltas across systems of the current embodiment (which are regulated to provide motive flow though analytics spools of these systems). They also allow for tracking of the distribution pressures required to transport the hydrocarbon/gas mixtures from the wells to their storage, processing, use, etc. locations.
  Casing pressures—These pressure measurement points are located at the well head/Christmas tree and monitor the various (if more than one( )) casing pressure of the well. They can be used to evaluate integrity issues and to diagnose atypical well behavior.
  High pressure temperatures—Co-located with the high pressure transducers. Allow tracking temperatures of the fluids prior to any pressure drops (which typically induce temperature drops as gases are released from the fluids)
  System temperatures—These temperatures allows for tracking of the temperature deltas across the high pressure planes, and allow for the estimation of the amounts of gas released from the fluids. As pressures decrease.
  System trunk flow meters—Total flow measured off of the well/process systems.
  Spool flow—flow measured though the analytics spools.
  ORP (Oxidation Reduction Potential)—measured in the analytics spools.
  pH—measured in the analytics spools.
  Conductivity—measured in the analytics spools.
  Corrosion—measured in the analytics spools.
  Dissolved O2—measured in the analytics spools.
  CO2—measured in the analytics spools.
  H2S—measured in the analytics spools.
  Fluid density—measured in the analytics spools and/or trunk spool.

In systems of some embodiments fluids enter the systems through input lines. Immediately after entering the systems/platform, system pressures, temperatures and flows are measured in the trunk spools. Downstream of the flow meters in the trunk spools are junction points where slipstreams are diverted into the analytics spool pipes. The analytics spools are pipes with larger diameter than the trunk spools (in the current embodiment). The size differences allow fluids that enter the analytics spools to separate (to some extent) into gaseous, hydrocarbon, and produced water layers. Such separation allows for more accurate measurements to be taken within the analytics spools and extends the lives and mean-time between calibrations of the sensors (by keeping them sensors from getting fouled by hydrocarbons or other materials for which they are not designed to operate within).

Motive flows though the analytics spools are produced via flow control valves located in the trunk spools and which are placed between the analytics spool input and analytics spool output connections. Furthermore, flow meters on the analytics spools allow for the flow velocities of the fluids in the analytics spools to be monitored and controlled. Thus, the flow meters allow systems of the current embodiment to achieve proper fluid separation and to provide sufficient crossflow velocities across the sensor tips thus minimizing, reducing, or eliminating fouling. The discharges from the analytics spools reenter the trunk spools downstream of the flow control valves. The discharge pressure transducers (downstream of the trunk spool flow control valves) allow for the pressure deltas across the systems/flow control devices to be monitored.

The analytics spool flow meters use calorimetric measuring principles to calculate flow velocities within the analytics spools. By measuring the signals from these flowmeters at varying pressure differentials, the flow velocities and, indications of water/oil ratios can be determined. This data can be used to regulate the flows within the analytics spools. Additionally, conductivity readings of the process fluids at different flow velocities are used to identify when adequate oil/water separation has been achieved. Once base line conditions have been recorded, deviations in produced water/hydrocarbon ratios with the process fluids can be estimated by monitoring spool flow readings, pressure deltas, and conductivity if desired.

Corrosion meters are also located in some analytics spools. These corrosion measurements monitors the corrosivity of the fluid passing through the analytics spools and are representative of corrosion rates that may be expressed in the flow lines. The data collected from the annulus pressure transducers and temperature gauges are used, in conjunction with the corrosion meter measurements and known well characteristics (i.e. depth), to estimate the rates of corrosion at different locations through the well bores in real-time (higher temperatures/pressures downhole typically translate into higher rates of corrosion). This capability (real-time measurements of annulus pressures, calculated hydrostatic pressures, estimated reservoir pressures and temperatures) allows for the identification of upset events that accelerate the rate of corrosion down hole that would typically not be recorded downstream of any pressure drops prior to fluid introduction into the flow lines. This data allows for the management of downhole and flowline corrosion via accurate modeling of conditions therein and potential application of chemistries required to manage those conditions on a feedback loop.

The dissolved oxygen probes of the current embodiment allow for the types of corrosion to be identified and/or estimated. For instance, if oxygen concentrations increase immediately after pump maintenance on a well, and decreases as the pump continues to operate, and the rate of corrosion during these intervals behaves in a similar fashion, and the pump pressure profile (as measured by the annulus pressure transducer) indicates a gradual increase in pressure, followed by a pressure plateau, it can be assumed that surface oxygen is leaking into the well and contributing to high rates of corrosion. Thus, these conditions can be linked to a mechanical failure in the well/pump equipment. Stable or gradually decreasing oxygen concentrations with a gradual decrease in recorded ORP coupled with a gradual increase in rate of corrosion suggest the presence of biologically induced corrosion. These calculations are used to influence well hardware maintenance and/or corrosion inhibitor/biocide dosage initiatives. Moreover, controllers of embodiments are configured to detect these conditions and to output signals indicative thereof.

Conductivity measurements are use, as mentioned above, to identify the degree of oil/water separation in the analytics spools of embodiments. Additionally conductivity readings are used to estimate the TDS (total dissolved solids), and thus, scaling potential of the process fluid. In conjunction with pH measurements, process temperatures, process pressures and laboratory analyses, the scale-forming potential of the fluids are monitored at different pressure planes to identify when, where, and what species are likely to precipitate out of solution using compound solubility curves. This data allows for dynamic application of anti-scalant applications when/where needed and in real-time (in accordance with embodiments and/or under the control of controllers of the current embodiment).

Paraffin accumulation rates are monitored by evaluating pressure, temperature and flow measurements observed over time (an in conjunction with established melting points for paraffin species observed in the process fluid). By evaluating these parameters, and the pumping pressure profile, paraffin accumulation in the wellbores and flowline/distribution systems can be identified by controllers of the current embodiment. This data is used by these controllers to generate signals indicative of potential needs to change solvent/paraffin inhibitor applications.

Trends in the observed process chemistries are used to, collectivity, identify when significant deviations in fluid compositions have occurred. These deviations are monitored by controllers of the current embodiment which create alerts that a sample should be collected for laboratory analysis. The results of these analyses are used to refine the algorithms/equations programmed into controllers of the current embodiment.

FIG. 1 illustrates an integrated process system. Generally, the system produces, gathers, refines (and/or processes), and/or distributes hydrocarbons. These hydrocarbons enter the system comingled with other fluids such as various gases and water. Many species can be found in the stream flowing through the system which include (but are not limited to) paraffins, asphaltenes, hydrates, hydrogen sulfide (H2S), oxygen, carbon dioxide, minerals (such as calcium, magnesium, boron, etc.) various salts, sand/dirt, bacteria, etc. Many of these species are desired and indeed the hydrocarbons therein usually possess economic value and are thus highly sought after.

But some species present problems at many points in the system. The water in the stream can be a nuisance, carry potentially detrimental compounds (including occluding and corroding agents) and in many cases must be disposed of. The paraffins, asphaltenes, and hydrates might precipitate out of solution at certain pressure/temperature points causing blockages. The oxygen and H2S can cause corrosion in certain regimes. Moreover, the latter gas is poisonous. Some of the minerals, furthermore can precipitate out of solution thereby creating scale on the internal surfaces of the tubes, pipes, and/or other components in the larger systems. Bacteria can colonize these internal surfaces (as well) creating a potential for biologic corrosion of these surfaces. Even the ordinarily sought after hydrocarbons can be problematic in that they can coat sensors, piping, equipment, etc. in the system thereby degrading their capability and/or render them useless.

Complicating matters further, the composition of the fluid in the system can vary with time and certainly varies as the fluid flows from point to point in the system. Sources of variation are too numerous to enumerate herein. But a few representative sources of these variations are as follows. For one thing, the reservoirs from which the fluid is drawn change with time. This variation can occur as the wells draw fluid thereby partially emptying some chambers/areas of the formation and thence drawing from other chambers.

Moreover, operators of the wells may perform re-work, maintenance, and/or stimulations on the wells. These operation can (intentionally) introduce chemicals into the system. The wells also have something of a life cycle. For instance, during drilling, the fluid flowing from the well will be largely drilling "mud." But, when the well reaches its production depth that fluid can begin carrying increasing quantities of hydrocarbons and the species consistent therewith. During completion of the wells, still other chemicals are introduced into the stream. Even when the wells have been placed in operation, stimulation and other work on the well can cause the chemistry of the produced fluid to vary (and often with no warning to those portions of the system downstream from the well).

Also, as the pressures, temperatures, pH, and other characteristics of the fluid change as it moves through the system, various species might precipitate out, off-gas, etc. To make matters still more complicated, the potential presence of so many species in the fluid renders many sensors inoperative, unreliable, imprecise, inaccurate, etc. Thus, operators of heretofore available systems have had to rely on sampling the fluid periodically and manually analyzing it to determine the species in the fluid, their concentrations, etc. and (hence) the likelihood that one or more problems might be occurring in the system (at, or near, the sample point).

With reference still to FIG. 1, and more specifically, the system 100 includes an upstream sector 102, a midstream sector 104, a downstream sector 106, wells 108, additive tanks 110, a controller 112, a gathering tank 114, refineries 116, point of use 118, pipes 120, a casing 122, a reservoir 124, a Christmas tree 125, a kill wing 126, a production wing 127, a pressure sensor 128, a temperature sensor 130, a flow meter 132, a choke 134, a trunk spool 136, an analytics spool 138, a tube 150, gases 152, hydrocarbons 154, water 156, a tube wall 158, corrosion 160, bacteria 162, a (paraffin) coating 164, and scale 166.

For the sake of convenience, those skilled in the art typically divide the system 100 into the upstream, midstream, and downstream sectors 102, 104, and 106 respectively. While the boundaries between these sectors are somewhat arbitrary, the upstream sector 102 generally comprises the wells 108, reservoirs 124, the additive tanks 110, and/or other equipment/objects in the "field" and/or closely associated with the production/retrieval of the hydrocarbons (including de-sanders, separators and valve assemblies). Conditions within the system 100 in the upstream sector 102 can vary widely. For instance, in the reservoirs 124, temperatures can exceed 400 degrees Fahrenheit with pressures reaching 2000 psi or more. Moreover, the fluid in the reservoirs 124 has yet to receive any treatment (at least initially) and has potentially many potentially problematic species in it.

In most situations, these fluids include a mixture of hydrocarbons (unless the wells were drilled to obtain other fluids) and usually some amount of water (often with salts dissolved therein). Needless to say, these conditions often present aggressive corrosion threats. Accordingly, many wells 108 comprise downhole instruments measuring the pressure, temperature, flowrate, and other parameters associated with the reservoir 124 (or at least the "bottom" of the well 108). Note that controllers 112 of embodiments can be in communication with these sensors (as well as sensors at other locations in the system 100) to obtain information therefrom.

As disclosed elsewhere herein, moreover, these conditions are not necessarily static. For one thing, as various areas, layers, volumes, formations, etc. associated with the reservoirs 124 are tapped, the varying fluid levels in the reservoirs 124 deliver fluids of varying composition to the well 108. At some times, predominantly hydrocarbons 154 might be flowing to the well 108 while, at other times, the predominant species might be water. And, at times and/or at particular wells, relatively high volumes of gas (for instance, methane) might be delivered to the well 108. Operator activity might also influence the species present in the comingled fluid. For instance, fracking might introduce a large proportion of water into the well 108 along with sand and agents which cause the fluid to "gel" thereby enabling the fracking operation. In other situations, operators might believe they have some issue to deal with in the formation. For instance, they might believe that some scale-creating agent has increased in concentration and, therefore they might inject an additive selected to combat that particular scale-related species. In addition, the reservoir characteristics may indeed change over time in developed fields as localized pressures decline, thus creating the potential for localized off-gassing, adiabatic temperature loss and thus precipitation and chemistry shifts.

As the produced fluid travels toward the surface through the casing 122 of a well 108 conditions change. For one thing, the pressure drops in the casing 122 as the hydrostatic head decreases. The fluid might also cool somewhat as the temperature of the surrounding formation drops (roughly with decreasing depth). The results include a potential effervescence of gases dissolved/entrained in the fluid. Moreover, the changing pressure/temperature point (as well as other changing conditions) might cause other species to precipitate out of solution.

As disclosed elsewhere herein, the additive tanks 110 can also be a source of changing fluid chemistry in the wells 108. While several such additive tanks 110 appear in FIG. 1, it is understand by those skilled in the art that these tanks are representative as a source of additives. While there are some situations in which one or more additive tanks 110 might be present near a well 108, additives are usually injected into a well (and hence brought to it) on an as-needed basis largely depending on the detected composition of the fluid therein. Nonetheless, these additives are usually injected into the well via the kill wing 126 of the Christmas tree/well head 125 although they could be injected by alternative means. That being said, such injections can be unscheduled and can occur without warning to user/operators downstream of the well 108.

The Christmas tree/well head 125 of a well allows many operations on the well 108 and also represents a point in the system 100 at which fluid conditions can change. For instance, additives might be injected into the reservoir 124 via the kill wing of the Christmas tree 125. Moreover, the fluid produced by the well 108 flows out of the annulus of the casing 122 through the production wing 127. More specifically, the production wing 127 often includes a choke 134 through which the produced fluid flows.

The choke 134 is used in many cases to maintain a back pressure in the casing 122 (and reservoir 124) to maintain a relatively constant/controlled flow of the fluid. The choke 134 also, as a result, causes a relatively large delta pressure across itself. Indeed, that delta pressure can be on the order of 800 psi or more. As a result, gas effervescence can occur with attendant fluid temperature decreases (as the gas expands). Accordingly, systems 100 of embodiments instrument the Christmas tree 125 with pressure sensors, temperature sensors, and flow meters (respectively 128, 130, and 132) which (along with downhole sensors) allow the amount of gas released to be estimated (via the Ideal Gas Equation and/or suitably modified versions thereof).

With ongoing reference to FIG. 1, the drawing illustrates the controller 112 positioned between a particular well 108 and a particular gathering tank 114. However, embodiments provide controllers 112 located elsewhere in the system 100 which are configured to sense conditions at these points as well as determining the composition of the fluid at those points. Moreover, while only one controller 112 is shown, multiple controllers 112 are within the scope of the disclosure and can be placed at each well 108, gathering tank 114, etc. Controllers 112 of the current embodiment comprise a trunk spool 136 and an analytics spool 138. The trunk spool 136 typically carries the bulk of the fluid flowing through the controller 112 while the flow control valve 140 thereof diverts a relatively small portion of the comingled fluid into the analytics spool 138. Note that the trunk spool 136 can comprise the flow control valve 140 such that any turbulence it might create fails to reach the analytics spool 138.

On that note, and with continuing reference to FIG. 1, the analytics spool 138 causes the fluid flowing therein to separate into layers of fluids with differing densities. It can do so in a number of different manners. For instance, the analytics spool 138 can be a relatively large diameter pipe such that the velocity of the fluid flowing therein slows (at least compared to that in the trunk poll 136) allowing turbulence to subside if not stop. Moreover, the analytics spool 138 can comprise an orifice, a pressure control valve, or other flow restriction that causes a relatively large pressure drop across itself. Thus, the pressure drop can cause further effervescence of gases entrained in the fluid. Meanwhile, the reduced fluid velocity in the analytics spool 138 can allow laminar flow to develop although even reduced turbulence will help the fluid species in the fluid to separate to some extent. Many embodiments, as is disclosed elsewhere herein, allow the fluid in the analytics spool 204 to slow sufficiently such that the conductivity sensor 218 begins sensing conductivity consistent with the presence of (mostly) water.

As a result, the fluid flowing in the analytics spool will separate into layers of gases 152, hydrocarbons 154, and water 156 among other materials. These layers will separate based on density in a gravity driven controller 112. However, such separation can be caused in other manners. For instance, the controller 112 could comprise a "cyclone" type separator such that centripetal forces cause the fluid to separate into such layers 152, 154, and 156 no matter the physical orientation of the analytics spool 138. No matter how the controller 112 causes the separation, that separation allows sensors to be positioned in the analytics spool 138 to sense conditions in the various major species (for instance, gases, hydrocarbons, water, etc.) for which they are designed to operate in while avoiding fouling by fluids in the other layers. In other words, the sensors can be "clocked" such that their active/sensing elements are likely to be in the fluids for which they are well suited to operate, thus extending their ability to accurately measure parameters over extended periods of time.

For instance, conductivity probes can be positioned where water (along with its dissolved electrolytes (such as salts) are expected to be. And, should readings from the conductivity sensors indicate that another fluid might be flowing across that sensor, the controllers 112 can reposition the flow control valve 140 to adjust the positions of those layers 152, 154, and 156. Thus, controllers 112 can be configured to position a variety of sensors 142 in fluids with which they are compatible and in which they can sense various chemistry-related conditions.

As a result, analytics packages 212 of various embodiments can sense the various species potentially in the comingled fluid, their concentrations, and various chemistry-related parameters (for instance pH). As a result, such analytics packages 212 can sense conditions which might lead to various issues such as those illustrated in FIG. 1 by tube 150. Tube 150 could be located at a number of locations in the system 100 including those in the upstream, midstream, and downstream sectors 102, 104, and 106. The species and conditions therein will vary with time and location. But, tube 150 illustrates some chemistry-related issues that might occur due to the chemistry of the process fluid.

For instance, certain species in the fluid might cause corrosion 160 of the tube wall 158 and this is true despite which layer 152, 154, and/or 156 of material might be in chemical contact with the tube wall 158 (or portion thereof). Bacteria 162 might become concentrated in a particular area on the tube wall 158 and cause corrosion thereof due to acids and other species produced by the bacteria 162. Furthermore, such corrosion 160 "under" or covered by the bacteria 160 might be mistaken for non-biologic corrosion absent further information pertaining to its cause (such as oxygen, carbon monoxide, H2S, etc. concentrations and their continuous time-based histories). Furthermore, paraffins and/or other materials might be precipitating out of solution and onto the tube wall 158. Certain minerals, moreover, might be forming scale 162 on the tube wall 158. Of course, and as disclosed elsewhere herein, the tube wall 158 of FIG. 1 is representative of various internal surfaces of the system 100 which might be affected by the chemistry of the fluid.

While FIG. 1 illustrates the controller 112 being located in the upstream sector 102 of the system 100 it could be located in the midstream and/or downstream sectors 104 and/or 106 respectively. For instance, controllers 112 could be placed before the gathering tanks 114 to identify which wells, fields, operators, etc. might be causing issues in the produced fluid being gathered in those tanks. Moreover, since conditions in the various refineries 116 of the system 100 can be "upset," controllers 112 can be placed therein to help identify various species in the fluids in those refineries 116 and/or the potential causes for changes therein.

Figure 2:
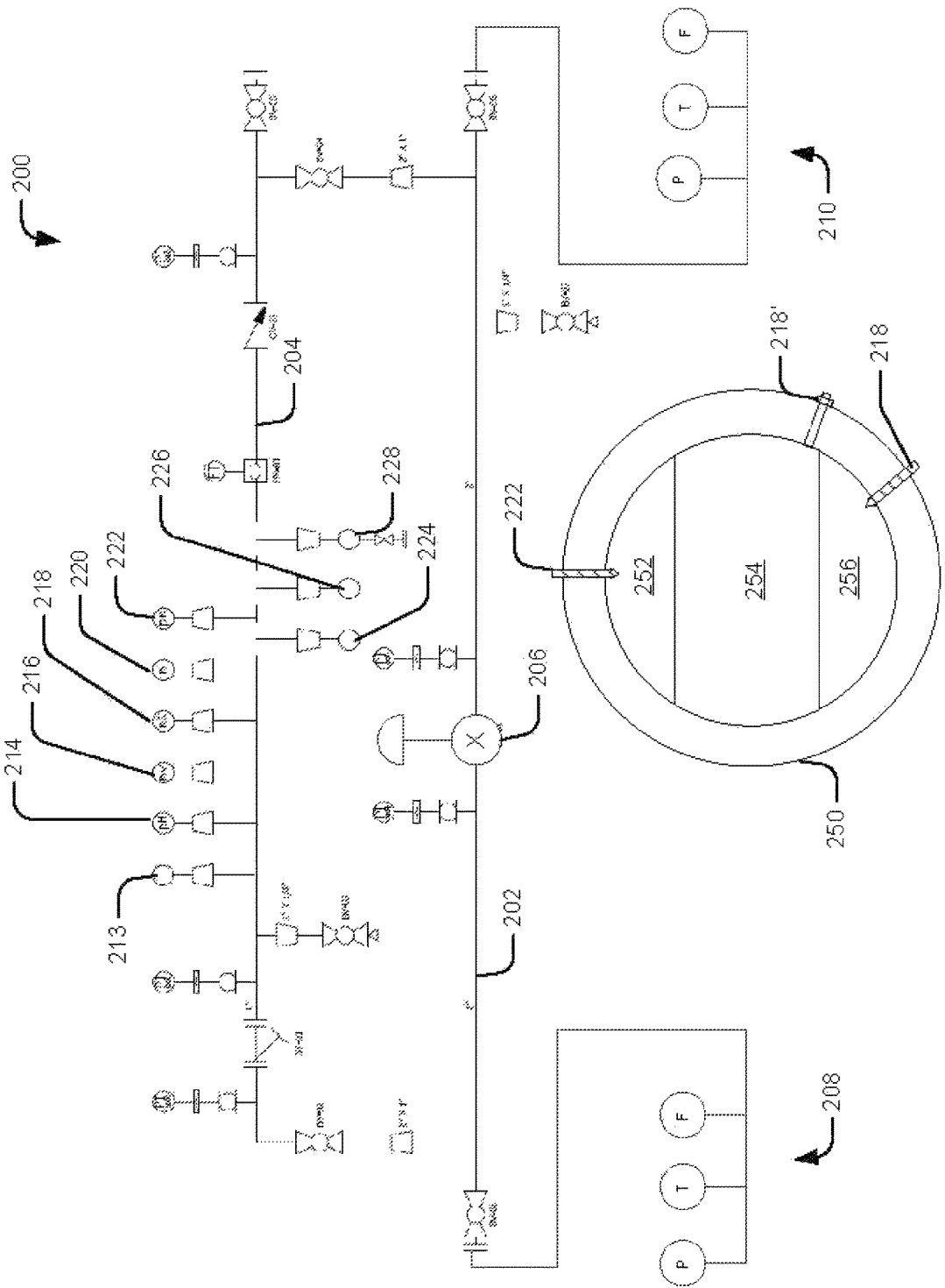
FIG. 2 illustrates a control system for a process system.

FIG. 2 illustrates a control system for a process system. Generally, the controller 200 senses chemistry-related conditions in process fluids and outputs indications thereof as well as control signals responsive to such conditions. For instance, controllers 200 of embodiments can sense whether gas, hydrocarbons, water, etc. are present in the controller 200 at locations corresponding to the sensors capable of relatively reliably, accurately, and/or precisely sensing conditions in those corresponding types of fluids. Moreover, with the layers of fluids in contact with the appropriate sensors, the controller 200 of embodiments senses the species in those fluids and outputs corresponding signals indicative thereof. Such controllers 200 can additionally, or in the alternative, output control signals to control corrective actions (such as chemical additions at appropriate locations in the system 100).

More specifically, FIG. 2 shows that the controller 200 of embodiments comprises the following: a trunk spool 202, an analytics spool 204, a flow control valve 206, upstream set of sensors 208, downstream set of sensors 210, an analytics package 212, a total dissolved solids (TDS) sensor 213, a pH sensor 214, an ORP (oxidation reduction potential) sensor 216, a conductivity sensor 218, a corrosion sensor 220, an oxygen sensor 222, a carbon dioxide sensor 224, an H2S sensor 226, and a biologic trap 228. Such combinations of instrumentation allow controllers 200 of the current embodiment to identify species likely to be comingled together in hydrocarbon process fluids. The analytics spool 204 comprises sensors for identifying species in the process fluid whereas the trunk spool 202 controls the flow of fluid through the analytics spool 204 as well as allowing most of the process fluid to flow through the controller 200.

The trunk spool 202 in many embodiments is approximately the same size as the process line to which the controller 200 mates. In contrast, the analytics spool 204 is a relatively large pipe which branches from, and parallels, the trunk spool 202. In addition to possessing a large cross-section, the analytics spool 204 possesses a length sufficient to allow the fluid flowing (albeit relatively slowly) therein to separate (at least partially) into the gas, hydrocarbons, and water layers 252, 254, and 256 respectively.

Thus, except for the flow control valve 206 (potentially), the controller 200 represents little in the way of head loss for a system 100 in which it might be installed. But the flow control valve 206 can be throttled to control the flow through the trunk spool 202 and hence the analytics spool 204. The flow through the analytics spool 204 can be rather slow as measured by linear velocity yet, because of its large size, it can provide enough flow to minimize any differential pressure across the controller 200.

As to the instrumentation of the controller 200 illustrated by FIG. 2, the two sets of sensors 208 and 210 allow the controller 200 to generally characterize the fluid flow. Each set of sensors 208 and 210 comprise a pressure sensor, a temperature sensor, and a flow meter. These sets of sensors can be a part of the controller 200 or can be external to it yet in (electronic) communication therewith. For instance, the well-based sensors 128, 130, and 132 can be considered as one of these sets and, likewise, other sets of sensors in the system 100 can be considered as one of the sensor sets 208/210.

Each set of sensors 208/210 defines a pressure "plane" at which enough information can be collected to estimate the amount of gas released from the process fluid between such pressure planes. In other words, there will be a set of pressure, temperature, and flow readings at each pressure plane. Generally, for any given pair of pressure planes, the sensed temperature will be higher for the upstream plane. And this is true whether the pressure planes are downhole, at the wellhead/Christmas tree, in or associated with the controller 200, or even downstream thereof. If a pressure drop occurs between pressure planes, a purely liquid fluid would experience a likely negligible temperature change. However, if the fluid contains significant gaseous species, those gases will expand and, hence, cool. Moreover, should one or more species vaporize due to the pressure drop, further cooling might occur. Using various gas equations (as modified for potential vaporization of real gaseous species likely to be in the comingled fluid), therefore, the controller 200 estimates how much gas expanded between the pressure planes.

With continuing reference to FIG. 2, it might now be helpful to consider the trunk spool 202 further. More particularly, the flow control valve 206 (or other flow control device such as an orifice, pressure control valve, etc.) plays a role in the ability of the controller 200 to sense species in the process fluid. More specifically, as the flow control valve 206 opens, more fluid flows through the trunk spool 202 and less through the analytics spool 204. The converse applies also: as the flow control valve closes, less fluid flows through the trunk spool 202 and more through the analytics spool 204. In the meantime, a sufficiently slow flow rate through the analytics spool 204 will allow time for at least some of the comingled species within the fluid flowing through the analytics spool 204 to separate by densities.

For instance, gases in the fluid can separate and form a gas layer 252 which (because of its low density) will appear above the fluid layers (that is, hydrocarbon layer 254 and/or water layer 256). Various gases might be in the gas layer 252 and will often include oxygen, carbon dioxide, water (or, rather, steam and/or water vapor), and/or other species such as H2S. Because, the gas layer 252 will be composed of gaseous species, the sensors positioned to sense conditions in that layer 252 can be configured to work in gaseous environments. In other words, such sensors can be located therein with minimal or, at least lessened chances, of being fouled by species not likely to be in the gas layer 252 in significant concentrations (notably, liquid hydrocarbons, water, species therein, etc.).

With ongoing reference to FIG. 2, hydrocarbons flowing to the controller 200 can also separate into a layer(s) such as hydrocarbon layer 254. Of course, the hydrocarbon layer 254 can contain a number of species of similar densities and/or those dissolved in (or otherwise comingled with) the predominate species in this layer (or layers). These species in the hydrocarbon layer 254 are comparatively predictable compared to the larger variety of species comingled in the process fluid flowing into the controller 200. Sensors can therefore be selected to sense these potential species and can be positioned with their active elements located in the likely location of the hydrocarbon layer 254. Moreover, because the hydrocarbon layer 254 segregates many species therein, there is a significantly improved likelihood that the sensors for that layer will not be fouled by species in the water layer 256 (and/or the gas layer 252).

Similarly, the water layer 256 can segregate species more likely associated with water than with hydrocarbons, gases, etc. And, again, sensors can be selected for sensing species in the water layer 256 that will enjoy a lessened chance of fouling (with species associated with the other layers). For instance, many salts will likely be found in the water layer 256 rather than the hydrocarbon layer 254 and/or the gas layer 252. Those sensors which are designed to work in the presence of salts can be positioned in the likely location of the water layer 256. Those sensors, moreover, which might be susceptible to salts can be positioned in positions likely to be in layers other than the water layer 256.

Dissolved salts, it is noted here, greatly increases the conductivity of water but not hydrocarbons (typically). Thus, the water layer 256 will typically be considerably more conductive than the hydrocarbon layer 254 and/or gas layer 252. Systems of embodiments use this distinction to detect where the water layer 256 exists and/or where other layers 252 and/or 254 might be present in the analytics spool 204. More specifically, if the conductivity sensor 218 senses (relatively low) conductive consistent with a layer of hydrocarbons (i.e., hydrocarbon layer 252), the controller can determine that the conductivity sensor 218 (or at least its active component) is located in the hydrocarbon layer 254. If, however, the conductivity sensor senses conductivity consistent with water (and/or salts potentially comingled therewith and therefore relatively high), the controller 200 of the current embodiment can determine that the conductivity sensor 218 is located in water.

Thus, the controller 200 can determine roughly where the water layer 256 lies and/or where the hydrocarbon layer 252 lies relative to the conductivity sensor 218. Moreover, the controller 200 can output an indication of whether the conductivity sensor 218 is in the water or hydrocarbon layer 256 or 254 respectively. Based on this indication, users can either leave the conductivity sensor 218 where it is (if it is in water) or move it to a differently clocked position 218' if it is determined to be located in hydrocarbons. In the alternative, or in addition, the controller 400 can adjust the position of the flow control valve 206 to alter the location/thicknesses of these layers 252, 254, and 256.

In the alternative, the flow in the analytics spool 204 need not be fully separated into water and hydrocarbons (and for that matter gases). Rather, the flow through it could be set (by the flow control valve 206) such that a partial separation occurs as the fluid flows from the upstream to the downstream side of the analytics spool 204. Thus, if the controller 200 determines that the conductivity sensor 218 is sensing hydrocarbons, the flow control valve 206 can be opened further to slow the flow in the analytics spool 204 thereby allowing greater separation to occur therein. When the sensors are determined to be operating reliably, the repositioning of the flow control valve 206 can be suspended.

Note that the other sensors in the analytics spool 204 can be positioned relative to the conductivity sensor 218 such that they are likely to be in a proper medium for their respective operation if the conductivity sensor 218 is sensing water. For instance, many common TDS sensors 213, pH sensors 214, ORP sensors 216, corrosion sensors 220, and dissolved oxygen sensors 222 do not perform well in the presence of hydrocarbons. These types of sensors can be clocked at locations in the analytics spool 204 (relative to the conductivity sensor 218) at which hydrocarbons will likely not be present. In the alternative, or in addition, sensors of types (which are compatible with hydrocarbons) can be positioned in the hydrocarbon layer 254 particularly if such measurements are desired in that layer. In the meantime, the carbon dioxide sensor 224 and H2S sensor 226 can be positioned where gas is expected to be present thereby also avoiding fouling issues. The biologic trap 228 can be positioned to capture potentially biologic material in the flow in any medium in which capturing biological specimens might be desired. For instance, the biologic trap 228 can be positioned to capture bacteria which might be present in the water layer 256.

In the alternative, or in addition, the controller 200 could include multiple conductivity sensors 218 at differing locations/heights in the system. Thus, the controller 200 can use the conductivity sensor(s) 218 that are located in water to gather data regarding the conductivity of that water. Those sensors which happen to be located in the hydrocarbons (or other potentially fouling layers for them) can be ignored. Moreover, because the controller 200 can determine which conductivity sensors 218 are in water (versus hydrocarbons), hydrocarbon fouling of the conductivity sensor 218 is not likely and its readings therefore enjoy improved reliability.

Thus, FIG. 2 illustrates a controller 200 which separates a received fluid into various media and has sensors positioned in those media for sensing various conditions therein in reliable, accurate, and precise manners in accordance with the current embodiment. As the fluid flows into the analytics spool 204, therefore, gases entrained in it, tend to expand, cool, and separate from the liquid components thereof. As the flow slows in the analytics spool 204, moreover, the heavier water separates from the hydrocarbons. As a result, the flow in the analytics spool 204 separates into generally three layers: the gas layer 252, the hydrocarbons layer 254, and the water layer 256. While complete separation of these media are not necessary for many embodiments, the degree of separation achieved can help the various sensors operate reliably.

And since the controller 200 of embodiments provides reliable, accurate, and precise measurements of the species/conditions present in the incoming, comingled fluid, an unexpectedly thorough understanding of that comingled fluid, its environment, and the environment they create can be determined. For instance, with the gases separated from the water and hydrocarbons, reliable measurements of the H2S, oxygen, and carbon dioxide in the incoming fluid can be determined. Furthermore, the pH can be obtained without fouling the pH sensor 214 and the ORP of the water can be determined (as well as its conductivity) with a minimal (or at least reduced) chance of sensor/instrument fouling.

Still with reference to FIG. 2, with reliable TDS measurements from the TDS sensor 213 (absent such fouling), various dissolved species can be identified in the incoming, comingled fluid. For instance, certain dissolved species will precipitate out of solution at particular pressure/temperature points. The controller 200 can identify which species might be precipitating between adjacent pairs of sensors. More specifically, given the temperature, pressure, and TDS measurements at two points in the controller 200, a change (decrease) in TDS between those measurements indicates that at least one species might have precipitated. By comparing the pressures and temperatures (and/or perhaps other pertinent conditions between the two sets of sensors—i.e. pH) to precipitation curves of various species, the controller 200 can infer that a particular species precipitated from solution. Moreover, if precipitation of that species can lead to scaling, fouling, etc., the controller 200 can signal that a particular anti-scaling agent (and/or other chemicals) should be injected (just) upstream of the location of the precipitation.

Furthermore, the corrosion sensor 220 can be used in ways heretofore not practicable. More specifically, the corrosion sensor 220 can be located in either water or hydrocarbons depending on which (or both) environments might be of interest from a corrosion perspective. If more than a user-selected amount of corrosion appears to be occurring in any layer, the controller 200 can also consider how much oxygen and H2S is present in the fluid. If one or both corrosive materials are present in larger than desired concentrations, the controller 200 can signal that appropriate chemicals be injected into the incoming comingled fluid to either scavenge or otherwise neutralize one or more particular corrosive species. Moreover, as well as or in the alternative, the controller 200 can compare the oxygen and carbon dioxide concentrations. If the oxygen concentration is increasing, the controller 200 can signal that an air leak into the system (from maintenance activities perhaps) might have occurred.

If the relative concentration of carbon dioxide is high or increasing, the controller 200 can signal that a biologic contamination might have occurred. Responsive thereto, users can check the biologic trap 228 for the presence of bacteria. If a relatively large concentration of bacteria 162 is found, that information can be entered into the controller 200 from which it can infer that biologic corrosion might be occurring (as opposed to inorganic corrosion) and the controller 200 can signal that (or direct that) an appropriate biocide be injected into the fluid. Of course, the detection of bacteria in the bacteria trap can be automated if desired.

Figure 3:
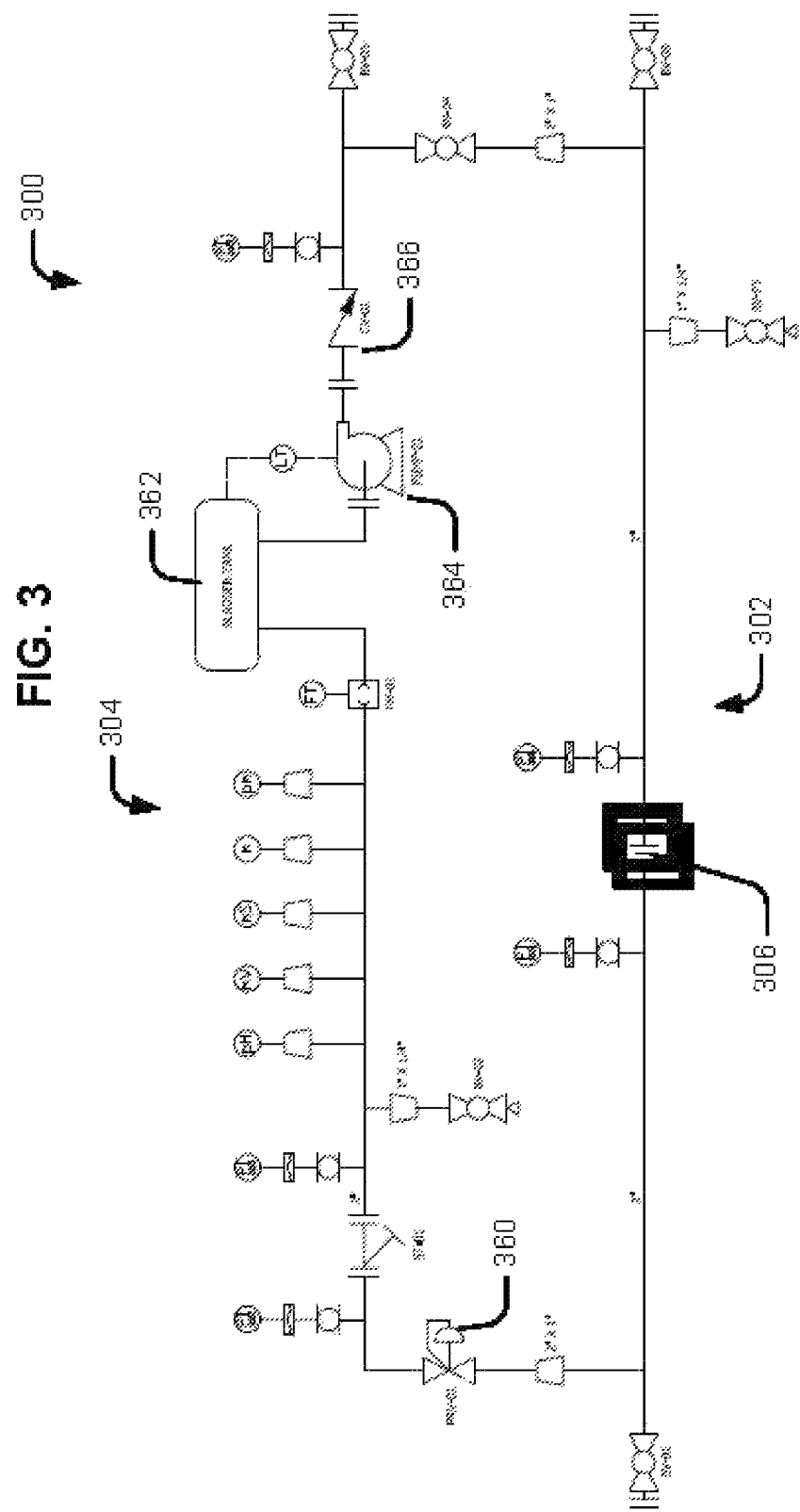
FIG. 3 illustrates a control system for another process system.

FIG. 3 illustrates a control system for another process system. Generally, the controller 300 shown in FIG. 3 can be used in portions of various process at which the internal pressures are relatively high. For instance, many transportation pipelines operate at elevated pressures to move materials from one place to another and in bulk. In contrast, the controller 200 shown in FIG. 2 can be used in places at which the systems operate at lower pressures. For instance, pressures in the "field," near the wells, tends to be rather low and fluid can be bled off if it without more than the flow control valve 206. Controller 300, in contrast, bleeds fluid from the process via a pressure control valve, analyzes it via an analytics spool, and injects the fluid back into the process via a pump 364.

Thus, as FIG. 3 shows, the controller of the current embodiment includes a trunk spool 302, an analytics spool 304, an orifice 306, a pressure control valve 360, a bladder tank 362, a pump 364, and a check valve 366. The orifice 306 serves to create a slight back pressure at the branch between the trunk spool 302 and the analytics spool 304 to help urge fluid to flow into the analytics spool 304. Although, in many embodiments, the orifice 306 can be omitted, or substituted with a control valve.

The controller 300 controls the pressure control valve 360 (and the pump 364) in a manner so that fluid is bleed from the process with a controlled pressure drop. Indeed, the controller 300 can control the pressure drop to 1) induce gases in the fluid to effervesce, 2) to cause various species to precipitate out of solution, and/or 3) to vary the locations of the gas, hydrocarbon, and/or water layers 252, 254, and/or 256. The controller 200 being configured to position those layers such that the various sensors will be in the fluids with which they are compatible. Of course, the controller 300 can use any of the available pressure sensors between the pressure control valve 360 and the pump 364 to control the pressure on the downstream side of the valve. It can also control the speed of the pump 364, in some embodiments, to vary the pressure and/or flow rate in the analytics spool 304 or portions thereof. Note that the bladder tank 362 helps smooth pressure/flow fluctuations in the analytics spool 304 while the check valve 366 prevents backflow of fluid from the process line or trunk spool 302 into the analytics spool 304.

Figure 4:
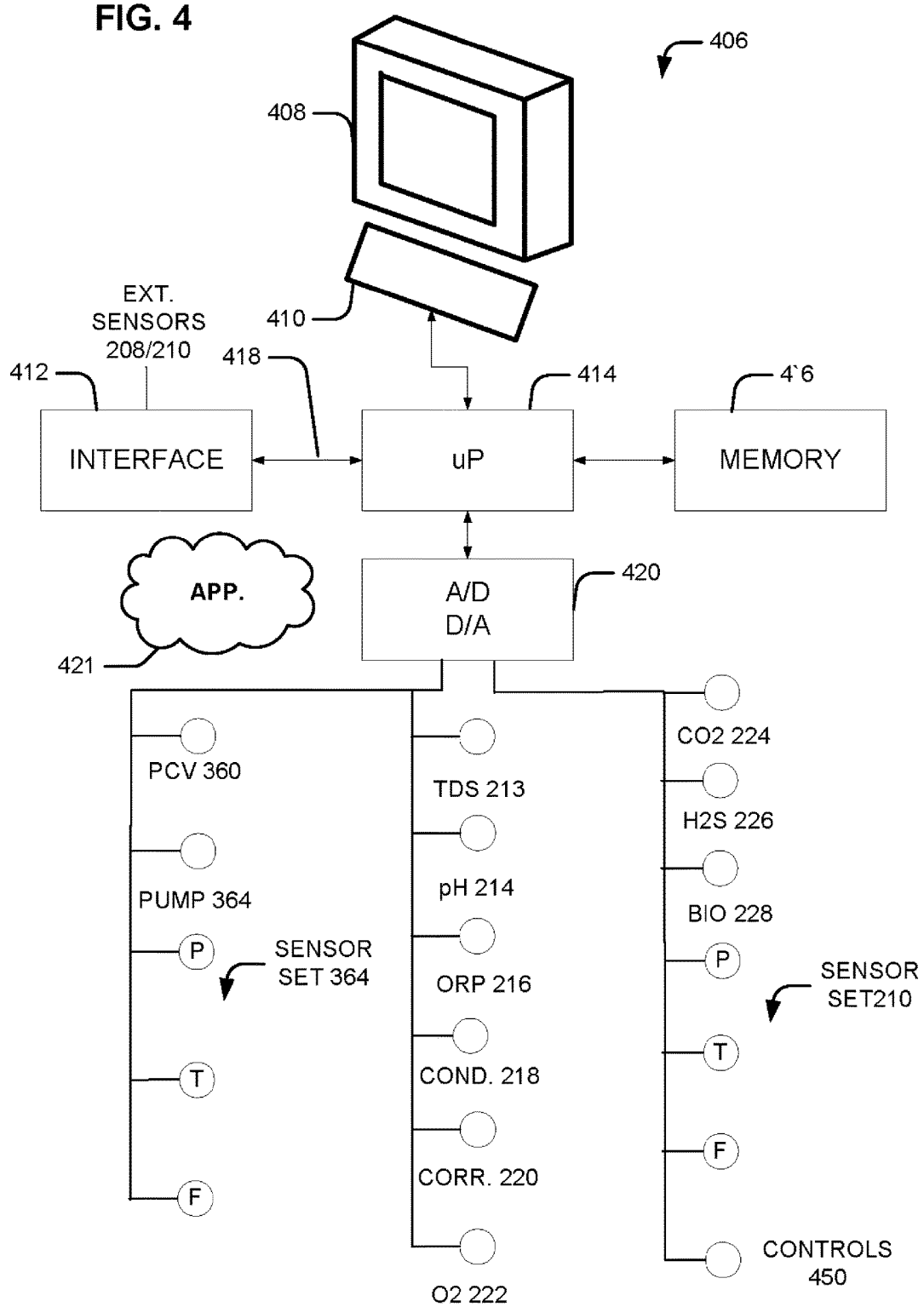
FIG. 4 illustrates a controller for controlling a process system.

FIG. 4 illustrates a controller for controlling a process system. A few words might be in order about the controller (s) 406 and/or other systems, apparatus, etc. used to control systems and/or perform methods in accordance with various embodiments. The type of controller 406 used for such purposes does not limit the scope of the disclosure but certainly includes those now known as well as those which will arise in the future. But usually, these controllers 406 will include some type of display 408, keyboard 480, interface 412, processor 414, memory 416, and bus 418. Nonetheless, these computers, when used as a controller 400 for systems/methods of embodiments are specially programmed to do so rather than being mere generic computers.

That being said, any type of human-machine interface (as illustrated by display 408 and keyboard 410) will do so long as it allows some or all of the human interactions with the controller 406 as disclosed elsewhere herein. Similarly, the interface 412 can be a network interface card (NIC), a WiFi transceiver, an Ethernet interface, cell connection, etc. allowing various components of controller 406 to communicate with each other and/or other devices. The controller 406, though, could be a stand-alone device without departing from the scope of the current disclosure.

Moreover, while FIG. 4 illustrates that the controller 406 includes a processor 414, the controller 406 might include some other type of device for performing methods disclosed herein. For instance, the controller 406 could include a microprocessor, an ASIC (Application Specific Integrated Circuit), a RISC (Reduced Instruction Set IC), a neural network, etc. instead of, or in addition, to the processor 414. Thus, the device used to perform the methods disclosed herein is not limiting.

Again with reference to FIG. 4, the memory 416 can be any type of memory currently available or that might arise in the future. For instance, the memory 416 could be a hard drive, a ROM (Read Only Memory), a RAM (Random Access Memory), flash memory, a CD (Compact Disc), etc. or a combination thereof. No matter its form, in the current embodiment, the memory 416 stores instructions which enable the processor 414 (or other device) to perform at least some of the methods disclosed herein as well as (perhaps) others. The memory 416 of the current embodiment also stores data pertaining to such methods, user inputs thereto, outputs thereof, etc. At least some of the various components of the controller 406 can communicate over any type of bus 418 enabling their operations in some or all of the methods disclosed herein. Such buses include, without limitation, SCSI (Small Computer System Interface), ISA (Industry Standard Architecture), EISA (Extended Industry Standard Architecture), etc., buses or a combination thereof.

More specifically, the controller 400 can be connected to the following instruments and controls: the upstream set of sensors 208, the downstream set of sensors 210, the (total dissolved solids) sensor 213, the pH sensor 214, the ORP sensor 216, the conductivity sensor 218, the corrosion sensor 220, the oxygen sensor 222, the carbon dioxide sensor 224, the H2S sensor 226, the biologic trap 228, the pressure control valve 360, the pump 364, and/or the control actuators 450 among others.

For instance, the controller 406 can sense the conductivity of the fluid in which the conductivity sensor 218 happens to be immersed and, from it, determine whether that conductivity sensor 218 is in water or hydrocarbons. Responsive thereto, the controller 400 can vary the position of the pressure control valve 360 and/or the speed of the pump 364 to expand/contract the water layer via residence time augmentation with a goal of maintaining the conductivity sensor 218 in an aqueous environment. And, by extension, maintaining the other sensors in environments (be it gaseous, hydrocarbon-based, aqueous, etc.) in which they are designed to operate. Moreover, the controller 406 can generate control outputs 450 in reliable, predictable, and repeatable manners not heretofore available for a variety of purposes. For instance, some control outputs 450 can be cautions, warnings, messages, etc. for the users of the controller 400 to take some action. In other situations, the control outputs 450 can include commands to various effectors to inject chemicals/agents into the controllers 200 and/or 300 and/or to affect other changes to the operations of the controllers 200/300.

Figure 5:
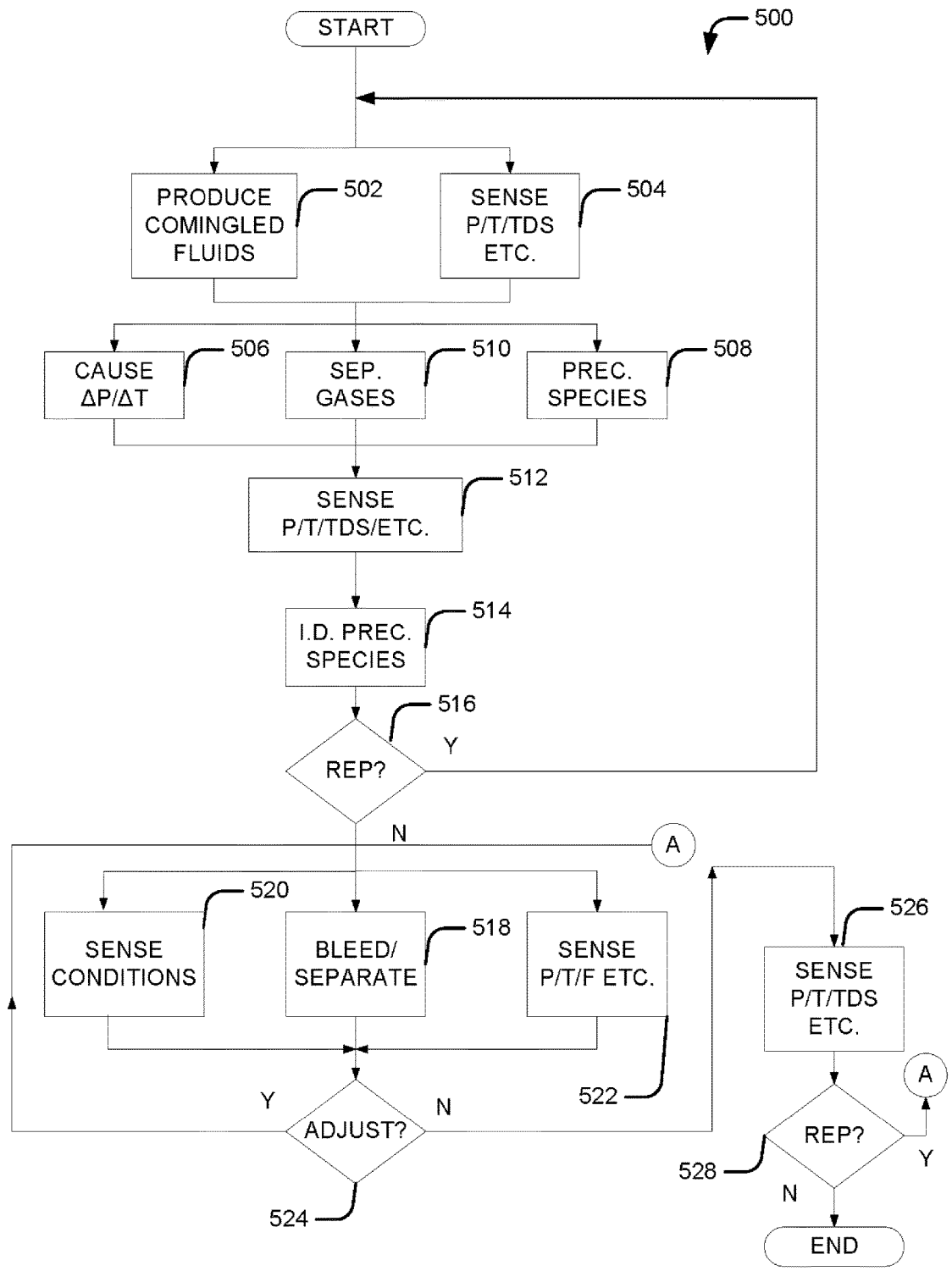
FIG. 5 illustrates a flowchart of a method of controlling a process system.

FIG. 5 illustrates a flowchart of a method of controlling a process system. Generally, the method 500 comprises causing comingled species in a process fluid to separate to some degree, positioning sensors (or adjusting the separation) to cause the sensors to operate in fluids (with which they possess compatibility), measuring properties of those (partially) separated fluids with those sensors, and (responsive thereto) identifying at least some of the comingled species. Method 500, in accordance with embodiments, includes various activities such as producing or otherwise obtaining a fluid with comingled species in it. These fluids can be mixtures of predominately hydrocarbons, water, and gases with other species contained in solution and/or dissolved therein to varying degrees. In many embodiments, these comingled fluids will flow from a well although they could occur at any location in a given process system whether "integrated" or otherwise. See reference 502.

The separation(s) of the fluid can occur at multiple locations in a system and pertinent conditions can be sensed both upstream and/or downstream of a various positions at which 1) a separation might occur and/or 2) at other locations of potential interest. For instance, in an integrated hydrocarbon production process, it might be of interest for a user to know certain conditions at the bottom of a well 108 and/or other "downhole" locations. The bottom conditions, of course, define an initial condition for the comingled fluid which generally exhibits high temperatures, high pressures, and a certain (perhaps varying) amount of total dissolved solids. Thus, the controller 200 or 300 can be instrumented with a set of downhole sensors comprising temperature, pressure, and TDS sensors among others. And, if desired, this set of sensors can communicate with the controller 406 via the interface 412.

Also, since this set of external set of sensors 208 might be exposed to rather extreme conditions and/or comingled hydrocarbons and water, they can be selected for such service environments. But, in many situations, the controller 406 will merely communicate with sensors chosen by operators of the well and will make such use of the measurements that they provide as is practicable. Nonetheless, as indicated at reference 504, pressure, temperature, and TDS measurements can be obtained at various downhole locations.

With continuing reference to FIG. 5, embodiments can cause (and/or take advantage of) pressure drops in the system. For instance, as the comingled fluid flows up through a well 108, it is known that its pressure drops (at least as a result of the corresponding reduction in hydrostatic "head" acting on the fluid). Moreover, some temperature decrease in the fluid might result because the fluid has flowed up from the relatively warm environment found in many subterranean reservoirs 124 toward the surface where generally cooler conditions exist. See reference 506.

As a result, some comingled species might precipitate from solution/suspension (see reference 508) causing a drop in TDS compared to deeper downhole locations. And, accordingly, TDS can again be measured at locations along the fluid's flow up through the well 108 to detect whether a change in TDS concentration has occurred between any pair of measurement points in the well 108. By comparing the pressure/temperature points of adjacent pressure planes with precipitation curves of species known/thought to be in the comingled fluid can allow controller 406 to identify species that might have precipitated out thereby causing the TDS decrease (see reference 514).

Depending on conditions in the well 108, though, it might be likely that at least some gas will effervesce from the comingled fluid during its movement up through the well 108. To detect how much gas might have effervesced, therefor, the pressure and temperature of the fluid at various locations closer to the surface can be taken. And, using the Ideal Gas Equation (potentially modified to account for likely conditions in the well) the amount of gas that effervesced can be estimated as indicated at reference 510. Of course, other pertinent conditions (for instance pH) can be sensed at such locations as well and used to refine the effervesced gas estimate(s). See reference 512.

Of course, such activities can be repeated at various locations in or associated with the well. In many situations, a choke 134 causes a pressure drop and possibly gas effervescence and/or species precipitation at the wellhead/ Christmas tree 125. But systems of embodiments can include other pressure drop inducing locations (such as across the pressure control valve 360) which can be instrumented to detect potential precipitations. Thus, as shown by reference 516, potential precipitations/effervescent events can be repeated at various locations in systems of embodiments.

With continuing reference to FIG. 5, method 500 can also (or in the alternative) include bleeding off a fraction of a comingled fluid to cause (at least partial) separation of its comingled species. For instance, in accordance with embodiments, method 500 can include bleeding off a portion of the comingled fluid using either flow control valve 206 (see FIG. 2) or pressure control valve 360 (see FIG. 3). In many scenarios bleeding off a portion of the fluid will cause various species to effervesce out, precipitate out, or otherwise separate. Additionally, the comingled fluid will typically separate into layers such as the gas layer 252, the hydrocarbon layer(s) 254, and/or the water layer 256 with one or more species precipitating out of one or more of these layers. Thus, FIG. 5 shows that method 500 can include measure the pressure, temperature, and/or TDS of the various layers (see reference 522). Moreover, other conditions associated with the layers formed from the comingled fluid can be sensed. Thus, pH, ORP, conductivity, corrosion rates, oxygen concentration, carbon dioxide concentrations, H2S concentrations, and/or biologic activity can be measured as indicated at reference 520.

With continuing reference to FIG. 5, the sensed conductivity in the analytics spool 204 can be used for various purposes besides simply measuring that conductivity. For instance, if the flow through the analytics spool 204 is too rapid for the layers 252, 254, and/or 256 to at least partially form upstream of the conductivity sensor 218, it is likely that the conductivity sensor 218 will sense a low conductivity (consistent with that of an oily/water mixture or perhaps even that of hydrocarbons). This result could be because the hydrocarbons surrounding the probe insulate it (relative to water) while, perhaps, also preventing the ions which might be dissolved in the comingled water from conveying charge through the mixed/comingled fluid.

Responsive to such a low conductivity, the controller 406 can adjust the position of the flow control valve 206 and/or pressure control valve 360 so as to slow the flow through the analytics spool 204 or 304 respectively. The slowed flow will therefore likely allow for greater separation to occur (at least with respect to the hydrocarbon layer 254 and the water layer 256). At some point the water layer 256 might develop sufficiently so as to engulf the conductivity probe. As a result, the water (which is likely to contain some concentration of salt-related ions as well as perhaps other conductive species) will cause the conductivity sensor 218 to sense a relatively large increase in conductivity. And from that conductivity increase, the controller 406 of the current embodiment can infer that water has been detected at the location of the conductivity sensor 218. Accordingly, the controller 406 can stop/slow the adjustment of the position of which ever valve (or other flow control device) it is using to control the flow through the analytics spool 204 or 304.

On the other hand, if the controller 406 encounters persistent low conductivity measurements despite using the full control authority of the pertinent flow control device, it can output a signal indicative thereof. Moreover, that signal can be configured to indicate that the conductivity sensor 218 can be moved to another location more likely to sense water in the analytics spool 204 or 304. In the alternative, or in addition, the controller 406 can check the conductivity sensed by other conductivity sensors 218 in the analytics spool 204 or 304 to determine whether they are sensing water. If so, the controller 406 can use the conductivity measurements from such a sensor(s) for further operations. See reference 524.

Once the controller 406 establishes sufficient separation between the hydrocarbon and water layers 254 and 256 (at the location of a conductivity sensor 218), it can sense other conditions in the now at least partially separated (and formerly, more comingled fluid). For instance, it can use measurements/information from the total dissolved solids (TDS) sensor 213, the pH sensor 214, the ORP sensor 216, the conductivity sensor 218, the corrosion sensor 220, the oxygen sensor 222, the carbon dioxide sensor 224, the H2S sensor 226, and the biologic trap 228 to identify which species are present in the comingled (but at least partially separated in the analytics spool 204) fluid as indicated at reference 526.

Figure 6:
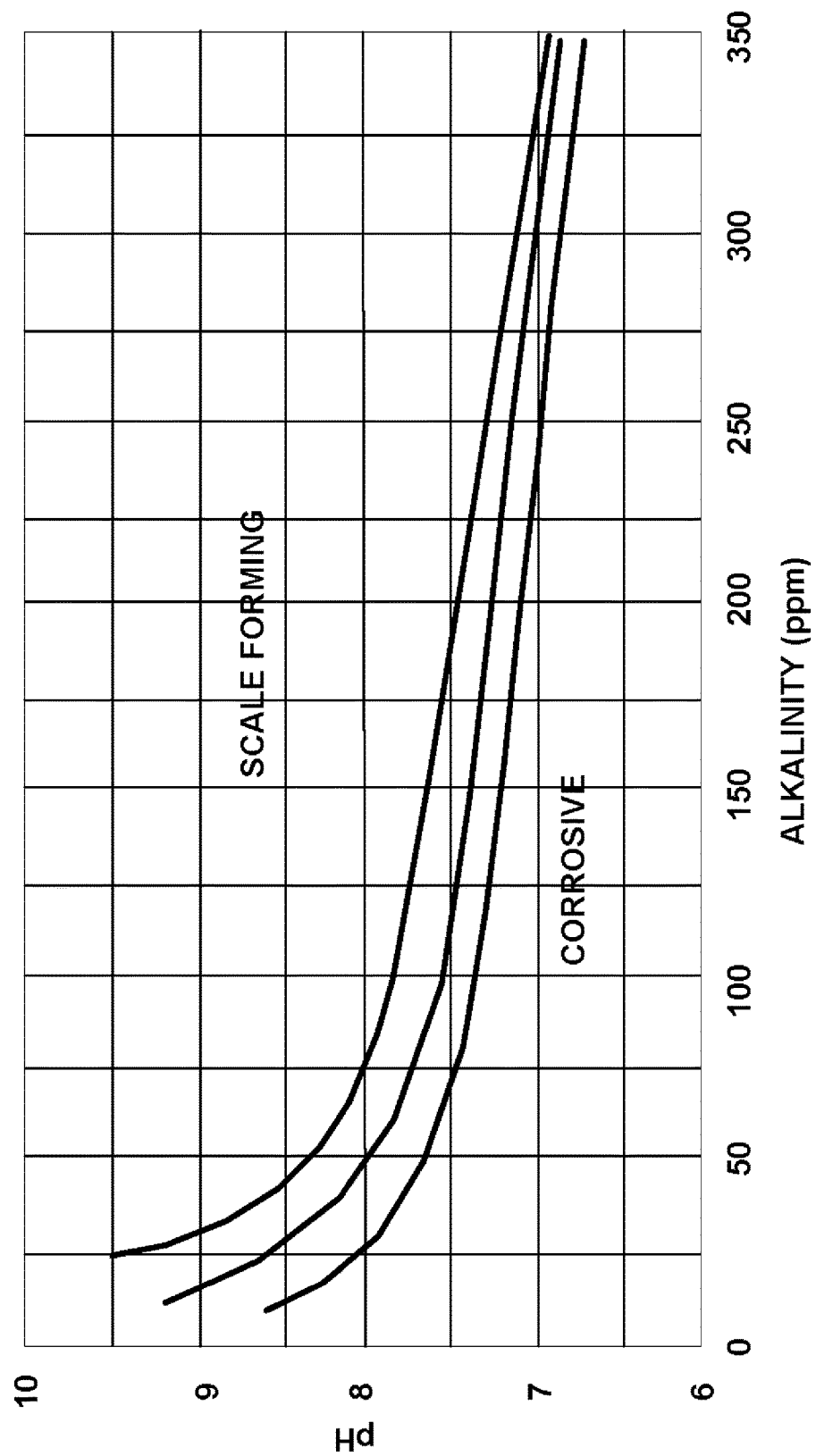
FIG. 6 illustrates a typical precipitation curve.
Figure 7:
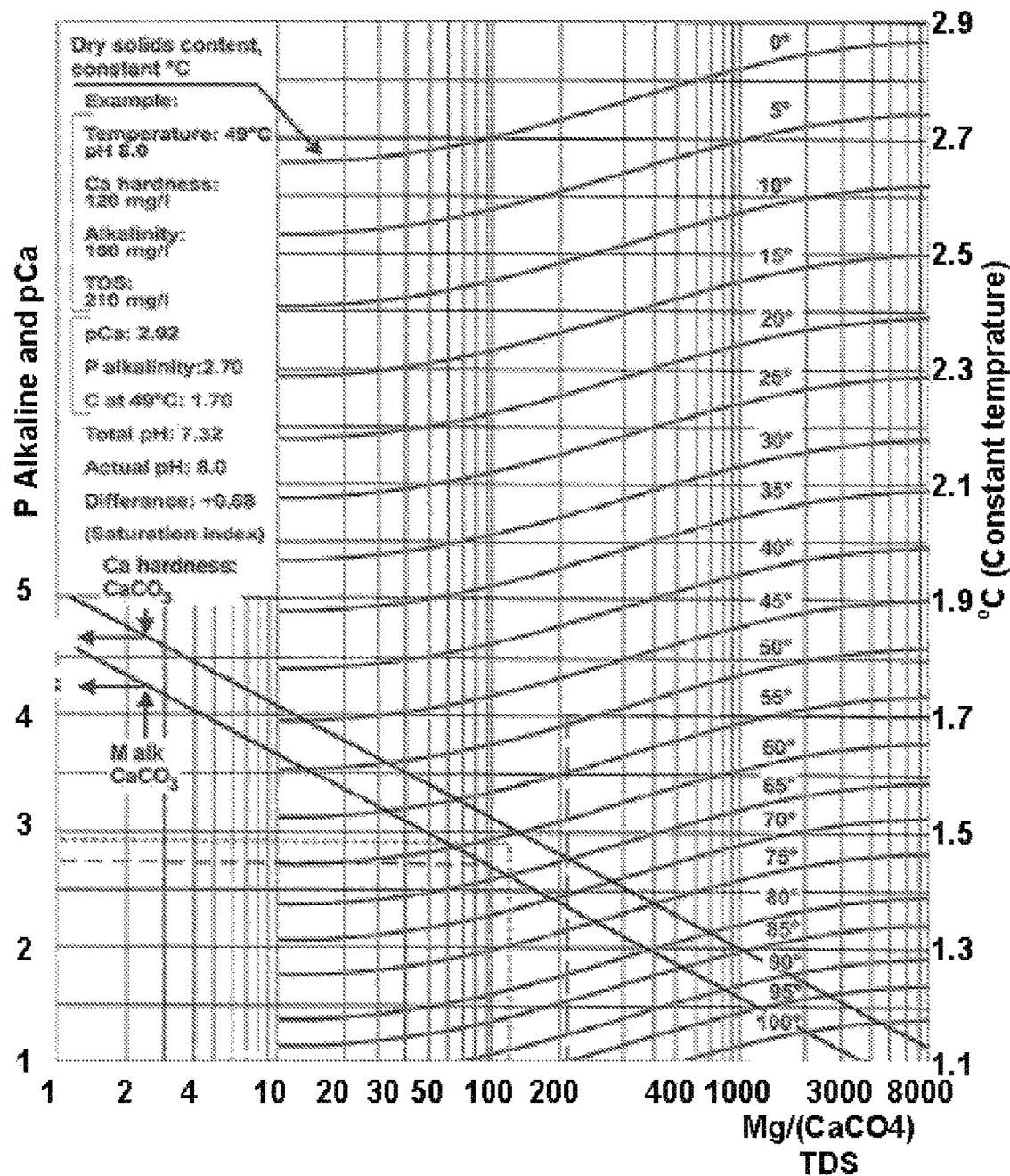
FIG. 7 illustrates another typical precipitation curve.

The pressure and temperature points associated with the analytics spool 204 and/or 304 (as well as other locations in the controller 200 or 300) can be compared to precipitation curves of species known to be in or likely to be in) the comingled fluid. FIGS. 5 and 6 illustrate typical precipitation curves against which conditions in the comingled fluid(s) can be compared to determine which species might be precipitating. The conductivity sensor 218 can be used to verify that ionic species might have precipitated. The TDS sensor 213 can be used to verify that other potentially-solid forming species (such as paraffins, asphaltenes, hydrates, etc.) might have precipitated.

Meanwhile, the various gas sensors can be used to determine whether biologic activity might be occurring in the comingled fluid. For instance, a change in the oxygen/carbon dioxide ratios in the comingled fluid (or separated gases) can indicate that bacteria 162 are consuming oxygen and producing carbon dioxide. ORP measurements from the ORP sensor 216 can contribute to such determinations as can measurements/information derived from the biologic trap 228. Of course, a detection of and/or increase in the H2S concentration (as measured by the H2S sensor 226) can indicate the presence/increase of sulfur reducing bacteria 162 in the comingled fluid. At the very least, the detection of H2S in the comingled fluid as sensed by the H2S sensor 226 can prompt the controller 406 to issue an alert to various users as to the presence of that hazardous material.

Furthermore, if the corrosion sensor 220 detects corrosion, the controller 406 can read the aforementioned gas sensors and/or the biologic trap 228 (or information derived therefrom) to make a determination as to whether the corrosion is biologic in nature or merely chemical in nature. The controller 406 can output signals indicative of these conditions and/or operate valves and/or other actuators to inject appropriate chemicals, agents, treatments, etc. into the controller 200 or 300 as might be appropriate.

Controllers of embodiments identify bacteriological proliferation and, more specifically, identify and mitigate MIC (Microbially Induced Corrosion). Such controllers 200/300 can implement methods which include establishing dynamic baseline fluid chemistries for given systems 100. Data collected and/or analyzed during these methods can be categorized into the following, high-level groups.

1) Characterization of the systems 100: for instance controllers 200/300 of the current embodiment can collect well depths, casing diameters, downhole temperatures, estimated geologic temperature lapse rates, pipeline length/diameter, etc. and store it in their memories 416 for further analysis.

2) Characterization of the process fluid: This type of data can be gathered every 300 ms (and/or at other rates) and can be used to model fluid dynamics through the systems 100 of interest:

Surface temperatures
Line temperatures (temperatures downstream of the back-pressure valves or other pressure planes)
Fluid temperatures in the controllers
Flow rates
Fluid densities
Water cut/oil cut ratios
Hydrocarbon API gravities
Annulus pressures
Casing pressures
Rat-hole/downhole pressures
Line pressures
Cross-flow velocities (at the sensors in the controllers 200/300)
Well power consumptions (if on artificial lift)

3) Characterization of fluid chemistry: This data can be gathered every 300 ms (and/or at other rates) and can be used to model fluid chemistries through systems 100 as flow rates, pressures, and temperatures change over time and/or with locations in the systems 100. The controllers 200/300 of the current embodiment can use composites of these metrics to "fingerprint" the fluid chemistries with reference to additional assay data collected via laboratory analyses. Such controllers are therefore able to identify relatively minute (and/or even larger) fluctuations in system chemistries over time and as they relate to overall conditions in the systems 100 and/or at specific locations therein. For instance, the following data can be collected at various points in the systems 100:

Conductivities of the water cuts
Dissolved oxygen concentrations
Dissolved CO2 concentrations
H2S (gas phase) concentrations
pH levels
ORP levels
Rates of corrosion (via high-speed ER probes, multielectrode array sensors, and/or other devices)

The foregoing data, furthermore, can be compared against/coupled with third party laboratory and/or biological assay data often collected concurrently with controller 200/300 installation and/or over the course of the deployment of the controllers 200/300 in a particular systems 100. With the fluid chemistries modeled at the measurement locations and perhaps throughout the systems 100, controllers 200/300 of embodiments use statistical analysis and/or event identification applications to identify when there deviations in various chemistry-related parameters might have occurred, are occurring, and/or might be expected to occur. Thus, at this juncture, it might be helpful to discuss MIC, how it typically manifests itself, what those manifestations precipitate, and, (from a data analysis prospective) what those manifestations look like over time and in response to different stimuli.

MIC is typically the result of SRB, APB (Acid Producing Bacteria), IRB (Iron Reducing Bacteria) or a combination of such species working in conjunction to impact infrastructure/equipment integrity. These species, moreover, directly impact fluid chemistry in specific ways and, typically do so at a geometric increasingly rates over time. In other words, it would be unusual to observe a step increase in MIC activity over a short time or, conversely, a MIC rate that remains steady (in the absence of countervailing conditions in the systems 100). Typically, bacteria of whatever type aggregate on (or colonize) specific locations of the walls of piping or production equipment (and typically, under scale layers). These "bio-slimes," therefore, typically create localized corrosion issues.

Controllers 200/300 of various embodiments therefore determine 1) whether bacteria are colonizing (or have colonized) their systems 100 and 2) whether the colonizations are causing MIC. Of course, therefore, controllers 200/300 sense corrosion (via direct/indirect measurement) and also sense the environments/chemistries in which that corrosion might be occurring.

Controllers 200/300 of embodiments are also configured to promote biological proliferation and/or bacteria surface adhesion at various points at which they sense corrosion. Thus biologic traps 228 thereof can define and/or comprise crevices, stagnation points, rough surfaces, porous surfaces, etc. attractive to bacteria of various types and comprise corrosion sensors 220 at those points. Moreover, controllers 200/300 of embodiments manage crossflow velocities at these points so as to further encourage bacterial colonization. As a result, controllers 200/300 of the current embodiment monitor corrosion at locations at which MIC will likely occur before they occur in other locations in the system 100.

In contrast, heretofore available coupons and/or corrosion measurement procedures fail to assure that MIC will occur at the point(s) where corrosions is measured. In other words, heretofore techniques cannot guarantee that the measurement device will be placed where a biofilm is likely to occur. They therefore either miss corrosion events and/or cannot identify whether any treatment regimen (that might have been) applied was successful and/or to what extent.

Furthermore, by tracking the rates of corrosion over time, controllers 200/300 can infer whether MIC or some other mechanism is likely to be causing the sensed corrosion in the biologic trap 228. More specifically, a slow corrosion rate that accelerates gradually (especially if exponential in nature) can indicate the presence of MIC. This scenario contrasts with oxidative, galvanic, and/or other forms of inorganic/electrochemical corrosion which typically varies with the concentration of the active species in the process fluid (and the corresponding temperatures/pressures if those conditions vary). Thus, controllers 200/300 of embodiments can compare the rates of change of various inorganic species with the rates of sensed corrosion to correlate (or not) such corrosion with these non-biologic species.

Such controllers 200/300 can also (or in the alternative) compare the rates of sensed corrosion elsewhere in the system 200 with the sensed corrosion in the biologic traps 228. If the potentially biologic corrosion rate increases whether the non-biologic species are varying, then the controllers 200/300 can infer that MIC is likely occurring (or likely to occur in the systems 100). Furthermore, by sensing other conditions indicative of bacterial presence (for instance, concentrations of H2S, oxygen, carbon dioxide, pH, their ratios, their rates of change, etc.), the controllers 200/300 can infer which types of bacteria might be present (for instance, SRBs, APBs, IRBs, etc.)

Corrosion, moreover, can be the result of several different processes, not just MIC. Controllers 200/300 of the current embodiment can, therefore, evaluate the environments in which corrosion might be occurring. For instance, the rate of corrosion they measure in surface-based portions of system 100 can be used in conjunction with the process variables (such as pressures, temperatures, flow rates, pH, etc.) to model corrosion rates which might be occurring downhole and/or in production equipment at differing pressure/temperature planes. In the case of inferred and/or suspected MIC, controllers 200/300 of embodiments monitor conditions for (minute) fluctuations in chemistry that would suggest the potential of biological proliferation.

For example, H2S concentrations in a sweet field (and/or increases thereof over time) suggest the presence of SRBs. Moreover controllers 200/400 can watch for shifts in oxygen and/or carbon dioxide concentrations, their ratios, pH, ORP etc. to identify whether SRB's, APB's and/or IRB's are present. These bacteria, as mentioned previously, impact fluid chemistry which controllers 200/300 can measure directly. Thus, such controllers can identify when it is likely that specific types of bacteria might be present in the systems 100.

Additionally, or in the alternative, controllers 200/300 of embodiments monitor what these chemical values do during non-pumping and/or offline intervals where flow slows down and/or stops. In a high flowing well, environment, or system 100 it can be difficult to sense minute changes in chemistry particularly with systems heretofore available. However, because controllers 200/300 of embodiments create environment in which the flow is relatively slow (and/or bacteria are encouraged to proliferate), during such off-cycles controllers 200/300 can monitor for (changes to) chemistry signatures that indicate the presence of bacteria.

For instance, when SRBs might be present, off cycles will likely produce a drop in ORP (as sulfur reduction reactions are electronegative), and an associated shift in pH as HCO3- is produced by these reactions. Additionally, data from bioassays from different collection times can be used by these controllers 200/300 to produce gross estimates of potential bacteria counts (and their types) and how they fluctuate over time (with reference to these chemistry shifts). As a result, controllers 200/300 can output signals indicative of the likely types/concentrations of bacteria present in the process fluid.

Moreover, controllers 200/300 of embodiments display the sensed conditions in the fluid in real-time. As stimuli (such as the injection of additives, maintenance, rework, etc.) are applied to various systems 100, their impacts can be observed in real-time. The absence of reactions to such stimuli can also be observed. If, for instance, users suspect that MIC exists and inject a corrosion inhibitor (instead of a biocide) into a system 100, the fluid conditions (i.e. the rate of corrosion) will often be observed to remain the same (except for any incidental changes that the inhibitor itself caused). On the other hand, the injection of a biocide, would cause an observable decrease in the rate of corrosion if that corrosion is caused by MIC reachable by the biocide.

In another scenario, if mineral scaling is occurring and causing a (partial) blockage, injecting a biocide (to attack bio-slime based fouling) would likewise cause no observable change in system 100 chemistry. That would, of course, be because the biocide would likely not manage the issue (even if MIC were present) because bacterial growths often occur under/behind mineral-based scales. But, the controller 200/300 can instead be configured to determine ( ) by examining conditions at various pressure planes and comparing them to various precipitation curves/models, that mineral-based scaling might be occurring (and that bacteria have colonized some part of the system/controller). Thus, the controller 200/3300 could output a signal responsive thereto that the injection of a corresponding anti-scalant would likely stop (and/or perhaps reverse) the scaling. That change, if it results following such treatment, would be observable via the sensed data displayed by the controller 200/300.

Furthermore, controllers 200/300 can be configured to cause scale to precipitate at the point of measurement. And/or controllers 200/300 can vary pressures in their analytics spools until precipitation occurs therein (at the point of measurement). Such features of controllers 200/300 of embodiments can cause worst-case (precipitation) conditions to occur in the analytics spools so that they can 1) identify issues early and 2) to obtain early feedback regarding the effectivity of applied corrective measures.

Thus, controllers of embodiments provide more data, information, analyses, corrective output signals, etc. than typical SCADA (Supervisory control and data acquisition)/WellWatcher packages. Indeed, controllers of embodiments provide information not heretofore available at least in any reliable, precise, repeatable, etc. manner. In accordance with embodiments, controllers transmit/send all the data they collect, generate, output signals, etc. to (centralized) databases for further analysis. Thus, additional treatment options can be identified, equipment problems can be identified, production data can be gathered, etc.

In some scenarios beam pumps outputting a data from dyno/downhole cards estimate fluid flows and cuts based on the pressure profiles of the pumping units (which rarely/never take into account variable water cut density and localized off gassing). In addition to capturing that data, controllers of embodiments obtain real-time flow, pressure, temperature, and power consumption measurements from wells/pumps. The resulting collections of data allow for more comprehensive and accurate representations of the performance of the wells and their equipment (for instance, evaluation of the pumps pressure/flow profile relative to the motors power draws can be used to identify motor fatigue and/or other equipment failures).

Additionally, or in the alternative, because this data is stored indefinitely, pumping/production trends can be characterized for various wells and used to balance pumping operations (and/or stimulation efforts) with reservoir capacities over time. One difference between previously available approaches and controllers of embodiments is that many previously available approaches provide "snapshots" of system operations at particular times. In contrast, controllers of embodiments provide a wealth of information, over time, that allow users to view a "video" of the information over extended time periods.

Embodiments have been disclosed which provide smart machines for identifying various chemical species in comingled process flows. Systems of some embodiments use cloud-based data management and analysis tools to monitor assets at local, geographic, and/or reservoir levels. The real-time acquisition and evaluation of data allows systems of some embodiments to continuously increase and/or maximize system efficiency and profitability.

Systems of various embodiments provide remote monitoring of the conditions in process streams. Such systems feature on-board cellular modems, SATCOM, and/or other telecommunication capabilities. All data collected by these systems can be streamed to (centralized) servers where it can be further analyzed and/or used to provide customers with customized user interfaces for their operations. In addition, or in the alternative, some systems provide real-time analytics. Such systems monitor fluid chemistries and dynamics in real-time, identify potentially problematic conditions within the fluids, and automatically apply chemistry to address those problems. Moreover, some systems possess robust designs. More specifically, some systems are built to operate in the harshest oilfield environments and monitor highly contaminated oilfield fluids reliably. Such systems can be deployed in Class 1, Div. 2, Class 1, Div. 1 environments, and can operate in high pressure environments.

The novel, non-obvious, and innovative approaches, systems, apparatus, and methods for production monitoring, management, and/or chemical treatment applications help users/companies with their well productivity and with maintenance of production equipment and hardware. Some embodiments, furthermore, incorporating a collection of techniques referred to herein as "fluid fingerprinting." Fluid fingerprinting allows systems of these embodiments to characterize fluid properties and mitigate potential problems. As fluid chemistries and dynamics are recorded in real-time, such systems identify fluid trends and identify fluid responses to chemical application regimes. The production chemistry values and analytic relationships across technologies allow for the fingerprinting of down-hole and pipeline conditions in accordance with embodiments. Such fingerprinting allows for the establishment of baseline conditions, and identification of changes resulting from different applied stimuli. Systems of embodiments comprise analytical sensors which apply composite metric analysis in order to help track and protect against: corrosion, hydrogen sulfide, bacteria, scaling, asphaltenes, paraffins, and/or hydrates.

Conclusion

Although the subject matter has been disclosed in language specific to structural features and/or methodological acts, it is to be understood that the subject matter defined in the appended claims is not necessarily limited to the specific features or acts disclosed above. Rather, the specific features and acts described herein are disclosed as illustrative implementations of the claims.

The invention claimed is:

1. An apparatus configured to fingerprint a fluid flowing from a hydrocarbon well, the fluid potentially including a time-varying mixture of gases, hydrocarbons, water, and various species therein, the apparatus comprising:
   an analytics spool;
   a flow control device configured to divert a flow of the fluid into the analytics spool, the analytics spool further being shaped and dimensioned such that the fluid to flow therein to separate into layers of materials with differing densities, some of the gases potentially separating from the fluid due at least in part due to a pressure drop, at least some of the hydrocarbons and water therein to separate at least in part due to the shape and dimensions of the analytics spool whereby a velocity of the fluid slows;
   a conductivity sensor positioned in the analytics spool at a position along the analytics spool and at a height at which the water is likely to being flowing, the conductivity sensor being configured to sense a conductivity of the fluid flowing at the position and height of the conductivity sensor and being further configured to generate a conductivity signal; and a controller in communication with the conductivity sensor and being configured, responsive to the sensed conductivity of the fluid to flow at the position and height of a conductivity sensor, to determine whether the fluid flowing at the position and height of the conductivity sensor is water.

2. The apparatus of claim 1 further comprising a pressure sensor, a temperature sensor, and a total dissolved solids/conductivity sensor all positioned at an approximately common position along the analytics spool and being in communication with the controller, the controller being configured to identify a pressure and temperate point at that common position responsive to corresponding signals from the pressure and temperature sensors, the controller being further configured to compare the pressure and temperature point to a plurality of precipitation curves for a corresponding plurality of species which are potentially in the fluid, the controller being further configured to determine whether the sensed total dissolved solids have changed and to output an indication responsive thereto that a particular species might be precipitating from the fluid.

3. An apparatus comprising:
an analytics spool;
a flow control device configured to divert a flow of fluid from a trunk line into the analytics spool, the analytics spool being configured such that the fluid to flow therein separates into layers of differing densities, the fluid flowing through the analytics spool and returning to the trunk line;
a sensor positioned in the analytics spool and being configured to sense a type of fluid flowing at the position corresponding to the sensor; and
a controller in communication with the sensor and being configured to output a signal indicative of the type of fluid flowing past the sensor;
a pressure sensor and a temperature sensor both positioned at an approximately common position in the analytics spool and being in communication with the controller, the controller being further configured to identify a pressure and temperature point at the common position responsive to corresponding signals from the pressure and temperature sensors, the controller being further configured to compare the pressure and temperature point to a precipitation curve for a species that is potentially in the fluid and to output a signal identifying a species of precipitate from the fluid.

4. The apparatus of claim 3 wherein the sensor is a conductivity sensor and is mounted on the analytics spool at a clocked position, the analytics spool further comprising a second clocked position adapted to receive the sensor.

5. The apparatus of claim 3 wherein the fluid is a mixture of hydrocarbons and water.

6. The apparatus of claim 3 further comprising one or more second sensors selected from the group further comprising a pH sensor, an oxidation reduction potential sensor, a conductivity sensor, an oxygen sensor, and a corrosion sensor.

7. The apparatus of claim 3 further comprising a carbon dioxide sensor and an oxygen sensor both being in communication with the controller, the controller being configured to determine an oxygen/carbon dioxide ratio responsive to corresponding signals from the carbon dioxide and oxygen signals, the controller being further configured to determine whether the ratio is changing over time and to output a signal of the ratio.

8. The apparatus of claim 3 further comprising a hydrogen dioxide sensor in communication with the controller, the controller being further configured to output a signal indicative of a concentration of hydrogen sulfide in the fluid flowing through the analytics spool.

9. The apparatus of claim 3 further comprising a bacteria trap which is configured to capture samples of biologic species potentially in the fluid.

10. The apparatus of claim 3 further comprising a pump positioned in the analytics spool and being configured to boost a pressure of the fluid to flow in the analytics spool.

11. The apparatus of claim 3 further comprising a flowmeter, a pressure sensor, and a temperature sensor located upstream of the analytics spool, the upstream sensors being in communication with the controller, the controller being further configured to compare signals from the upstream sensors with corresponding signals from sensors downstream in the apparatus, the apparatus further comprising a total dissolved solids/conductivity sensor in communication with the controller, the controller being further configured to sense a change in the total dissolved solids and to determine from the comparison of the upstream and corresponding downstream signals which species might have precipitated out of the fluid between the upstream and downstream sensors.

12. The apparatus of claim 3 further comprising an interface configured to receive signals from a well indicative of a pressure, a flow rate, and a temperature of the fluid flowing from the well, the interface being in communication with the controller, the controller being further configured to compare the signals from the well sensors with corresponding signals from sensors downstream in the apparatus, the apparatus further comprising a total dissolved solids sensor in communication with the controller, the controller being further configured to sense a change in the total dissolved solids and to determine from the comparison of the well and corresponding downstream signals which species might have precipitated out of the fluid between the well and downstream sensors.

13. The apparatus of claim 3 further comprising a corrosion sensor and a biological activity sensor configured to sense potential biological activity, the corrosion and biological activity sensors being in communication with the controller, the controller being further configured to output a determination of whether corrosion sensed by the corrosion sensor is biological in nature.

14. The apparatus of claim 3 wherein the analytics spool is configured such that the fluid to flow therein separates into layers of differing densities by being shaped and dimensioned to create a pressure drop in the fluid and a slowing of velocity of the fluid.

15. A method of fingerprinting a fluid, the fluid potentially including a time-varying mixture of species therein, the method comprising:
diverting a portion of the flowing fluid into an analytics spool from a trunk line;
causing the fluid in the analytics spool to separate into layers of differing densities due to a shape and dimensions of the analytics spool;
sensing a type of fluid flowing at a position in the analytics spool where a layer of water is expected to flow using a sensor;
returning the fluid in the analytics spool to the trunk line; and outputting a signal indicative of the type of fluid at the position along the analytics spool at which water is expected to flow using a controller in communication with the sensor;

sensing a pressure, a temperature, and a total dissolved solids concentration at an approximately common position relative to the analytics spool using corresponding sensors;

identifying, responsive thereto, a pressure and temperature point at the approximately common position using the controller;

comparing the pressure and temperature point to a plurality of precipitation curves for a corresponding plurality of species that are potentially in the fluid using the controller;

determining whether the sensed total dissolved solids concentration has changed using the controller; and outputting an indication responsive thereto that a particular species might be precipitating from the fluid using the controller.

16. The method of claim 15 further comprising changing a position of the sensor responsive to the sensed type of fluid.

17. The method of claim 15 further comprising sensing a pH, an oxidation reduction potential, a conductivity, an oxygen concentration, and a corrosion rate in the fluid using a corresponding set of sensors.

18. The method of claim 15 further comprising:
sensing a carbon dioxide and an oxygen concentration in the fluid using a corresponding pair of sensors;
determining whether a ratio between the carbon dioxide and oxygen concentrations has changed; and
outputting a signal of the ratio.

19. The method of claim 15 further comprising sensing a hydrogen sulfide concentration in the fluid and outputting a signal of the hydrogen sulfide concentration.

20. The method of claim 15 wherein step of causing the fluid in the analytics spool to separate into layers of differing densities due to a shape and dimensions of the analytics spool further comprises the step of creating a pressure drop for the fluid and slowing the velocity of the fluid.

* * * * *